(12) United States Patent
Khomami Abadi et al.

(10) Patent No.: US 10,386,379 B1
(45) Date of Patent: Aug. 20, 2019

(54) CHEMICAL SENSING SYSTEM

(71) Applicant: Stratuscent Inc., Montreal (CA)

(72) Inventors: Mojtaba Khomami Abadi, Montreal (CA); Amir Bahador Gahroosi, Montreal (CA); Matthew V. Gould, Montreal (CA); Ashok Prabhu Masilamani, Montreal (CA)

(73) Assignee: Stratuscent Inc., Montreal (CA)

( * ) Notice: Subject to any disclaimer, the term of this patent is extended or adjusted under 35 U.S.C. 154(b) by 0 days.

(21) Appl. No.: 16/261,195

(22) Filed: Jan. 29, 2019

Related U.S. Application Data

(60) Provisional application No. 62/623,440, filed on Jan. 29, 2018.

(51) Int. Cl.
  *G01N 35/00* (2006.01)

(52) U.S. Cl.
  CPC ........... *G01N 35/00722* (2013.01); *G01N 2035/00891* (2013.01)

(58) Field of Classification Search
  CPC .............. G01N 35/00722; G01N 2035/00891
  USPC ............................................................ 702/23
  See application file for complete search history.

(56) References Cited

U.S. PATENT DOCUMENTS

| | | | |
|---|---|---|---|
| 6,882,940 B2 * | 4/2005 | Potts | A61B 5/14532 435/14 |
| 7,640,116 B2 | 12/2009 | Duong et al. | |
| 7,858,720 B2 | 12/2010 | Ryan et al. | |
| 8,024,113 B2 | 9/2011 | Homer et al. | |
| 8,024,133 B2 | 9/2011 | Homer et al. | |
| 8,187,865 B2 | 5/2012 | Yun et al. | |
| 8,338,552 B2 | 12/2012 | Ryan et al. | |
| 9,080,942 B2 | 7/2015 | Zhong et al. | |
| 2009/0079977 A1* | 3/2009 | Lipson | A61B 5/0059 356/301 |
| 2019/0027249 A1* | 1/2019 | Fuksenko | G16H 50/50 |

OTHER PUBLICATIONS

Hao Zhang, Itza Mendoza-Sanchez, Eric L. Miller, Fellow, IEEE, and Linda M. Abriola, "Manifold Regression Framework for Characterizing Source Zone Architecture"., IEEE Transactions on Geoscience and Remote Sensing, vol. 54, No. 1, Jan. 2016 (Year: 2016).*

* cited by examiner

*Primary Examiner* — Yoshihisa Ishizuka
(74) *Attorney, Agent, or Firm* — Wolf, Greenfield & Sacks, P.C.

(57) ABSTRACT

A chemical sensing system is described. The chemical sensing system can include a plurality of sensors arranged on at least one substrate. The sensors may have differing sensitivities to sense different analytes, and may each be configured to output a signal in response to sensing one or more of the different analytes. The chemical sensing system can further include a computer processor programmed to receive the signals output from the plurality of sensors. The computer processor may be further programmed to determine a concentration of analytes in the sample based, at least in part, on the received signals and a model relating the signals or information derived from the signals to an output representation having bases corresponding to analytes.

30 Claims, 11 Drawing Sheets

CHEMICAL SENSING SYSTEM

RELATED APPLICATIONS

This application claims priority under 35 U.S.C. § 119(e) to U.S. Provisional Application 62/623,440, entitled, "Systems and Methods for Accurate Estimation of Concentration of Selected Fluid Analytes in Open Environments," filed Jan. 29, 2018, the entire contents of which is incorporated by reference herein.

BACKGROUND

Direct and indirect interactions with chemicals in the environment can adversely affect human physical and mental health. Chemicals in the environment may include, for example, particulates and volatile organic compounds ("VOCs") generated at hospitals, chemicals emanating from food spoilage, VOCs exhaled in breath, industrial and automobile exhausts, and early indications of processes such as disease, food spoilage, and combustion.

SUMMARY

Aspects of the present application relate to a real-time, low-cost, low-power, miniature chemical sensing system capable of simultaneously sensing multiple chemicals. The system includes a component, which may be a sensor chip, that contains an array of nanocomposite sensors. These sensors are configured to produce a unique fingerprint for any given chemical or combination of chemicals. Each nanocomposite is, in general, sensitive to a particular chemical (e.g., ammonia), but is also cross-sensitive to other chemicals (e.g., acetone, carbon dioxide). Although individual sensors may lack high selectivity, an array of sensors formed from the combination of cross-sensitive polymers can generate a response pattern specific to a particular chemical combination. This approach allows for targeting a broad range of chemical analytes for identification and quantification. Additionally, this approach allows for creating large, centralized reference databases of chemical fingerprints, which can then be used to train machine-learning models capable of deconvolving the fingerprint of a complex mixture of chemicals.

Some embodiments include a chemical sensing system including a plurality of sensors arranged on at least one substrate. A first sensor and a second sensor of the plurality of sensors have different sensitivities to sense at least one analyte in a sample. Each of the plurality of sensors can be configured to output a signal in response to sensing the at least one analyte. The chemical sensing system also includes a computer processor programmed to receive the signals output from the plurality of sensors and determine a concentration of the at least one analyte in the sample. This determination can be based, at least in part, on the received signals and a model relating the signals or information derived from the signals to an output representation having bases corresponding to analytes. These analytes can include the at least one analyte.

In some instances, the model can include a first model relating the signals output from the plurality of sensors to a feature representation. The model can also include a second model relating the feature representation to the output representation.

In various instances, the first model can include a mapping from the signals to response values and a weighting relating the response values to the feature representation. The weighting can include weights of a recurrent neural network or convolutional neural network that relate the response values to the feature representation. The mapping can assign to each response value an amplitude characteristic and/or a temporal characteristic of a corresponding signal. The amplitude characteristic can include a normalized change in an amplitude of the corresponding signal. The temporal characteristic can include a rise time or a fall time of an amplitude of the corresponding signal.

In some instances, a change in a location of a point in the feature representation corresponding to an analyte concentration in the sample can be a non-linear function of a change in the analyte concentration in the sample.

In various instances, the second model relating the feature representation to the output representation can include a first sub-model relating the feature representation to a latent representation. The latent representation can have a lower dimensionality than the feature representation. The second model relating the feature representation to the output representation can include a second sub-model relating a latent representation to a straightened orthogonal representation. In some instances, one-dimensional manifolds in the straightened orthogonal representation corresponding to varying concentrations of a same analyte have zero angle between them. In various instances, one-dimensional manifolds in the straightened orthogonal representation corresponding to different analytes are orthogonal.

In some instances, the second model relating the feature representation to the output representation can include a third sub-model relating a straightened orthogonal representation to the output representation. The third sub-model can relates the straightened orthogonal representation to a non-linearized output representation having standard bases associated with the analytes. The third sub-model can also relate the non-linearized output representation to the output representation. A change in a location of a point in the output representation corresponding to an analyte concentration in the sample can be a linear function of a change in the analyte concentration in the sample. In some instances, each signal can include a time series of measurements.

In various instances, the model can include a device-specific model relating the signals or information derived from the signals to an intermediate representation. The model can also include a device-independent model relating the intermediate representation to the output representation.

Some embodiments include a chemical sensing system having at least one computer processor and at least one computer readable medium. The at least one computer readable medium can contain instructions that, when executed by the at least one computer processor, cause the chemical sensing system to perform a training process. The training process can include receiving a training dataset generated by a plurality of sensors having different sensitivities to sense at least one analyte in a sample. Each of the plurality of sensors can be configured to output a signal in response to sensing the at least one analyte. The training process can also include training, using the training dataset, an assessment model relating the signals and/or information derived from the signals to an output representation having bases corresponding to analytes. The analytes can include the at least one analyte in the sample. The training process can include configuring the chemical sensing system to detect concentrations of the analytes using the trained assessment model relating the signals or information derived from the signals to the output representation.

In some embodiments, training the assessment model can include generating a first model relating the signals output from the plurality of sensors to a feature representation and generating a second model relating the feature representation to the output representation. Generating the first model can include training weights in a recurrent neural network or convolutional neural network using the training dataset. The training can be performed using an unsupervised learning technique.

In some instances, generating the second model relating the feature representation to the output representation can include generating a first sub-model. The first sub-model can relate the feature representation to a latent representation having a dimensionality less than the dimensionality of the feature representation. Generating the first sub-model can include training weights in an autoencoder or generative adversarial network using the training dataset. The training can use an unsupervised learning technique.

In some instances, a continuous manifold embedded in the feature representation can contain the signals output from the plurality of sensors. The continuous manifold can have a dimensionality equal to the dimensionality of the latent representation. Generating the first sub-model can include relating the continuous manifold to the latent representation.

In some instances, training the assessment model can include automatically identifying manifolds corresponding to samples of varying concentrations of a same analyte using local gradient changes in the feature representation.

In various instances, generating the second model relating the feature representation to the output representation can further include generating a second sub-model relating the latent representation to a straightened, orthogonal representation. Generating the second sub-model can include training at least one neural network using the training dataset and at least one loss function. The at least one loss function can be configured to penalize non-zero angles between vectors output by the at least one neural network that correspond to samples of varying concentrations of a same analyte. The at least one loss function can also be configured to penalize non-orthogonal vectors output by the at least one neural network that correspond to samples of different analytes.

In some instances, the at least one neural network can include a first feedforward neural network that relates the latent representation to a straightened representation. The at least one neural network can also include a second feedforward neural network that relates the straightened representation to a straightened, orthogonal representation. Training the at least one feedforward neural network can include training the first feedforward neural network and/or the second feedforward neural network using an unsupervised learning technique.

In various instances, generating the second model relating the feature representation to the output representation can further include associating bases in the straightened orthogonal representation with the analytes.

In some instances, generating the second model relating the feature representation to the output representation can further include generating a third sub-model that relates the straightened orthogonal representation to the output representation. Generating the second model relating the feature representation to the output representation can further include associating bases in the straightened orthogonal representation with the analytes using labels in the training data; generating an introduction model that introduces the associated bases onto the standard bases of a non-linearized output representation; and generating a linearizing model that linearizes the non-linearized output representation using concentrations in the training data. In some aspects, the linearizing model that linearizes the non-linearized output representation comprises at least one feedforward neural network trained to linearize the non-linearized output representation using the training data and concentration values corresponding to the training data. In some instances, training the an assessment model can include receiving a device-specific model trained to relate signals acquired by another chemical sensing device to an intermediate representation and retraining the trained device-specific model using the training dataset. Training the assessment model can also include receiving a device-independent model trained to relate the intermediate representation to the output representation and composing the retrained device-specific model with the device-independent model to generate a trained assessment model.

Some embodiments include an additional chemical sensing system. This chemical sensing system can include a plurality of sensors arranged on at least one substrate. A first sensor and a second sensor of the plurality of sensors can have different sensitivities to sense at least one analyte in a sample. Each of the plurality of sensors can be configured to output a signal in response to sensing the at least one analyte. The chemical sensing system can also include a computer processor programmed receive the signals output from the plurality of sensors and determine a location in a latent representation using a homeomorphic map. The homeomorphic map can relate the signals or information derived from the signals to locations in the latent representation. The computer processor can further be programmed to identify locations in the latent representation in a neighborhood of the determined location and determine concentrations of one or more analytes in the sample. This determination can use known concentrations of one or more analytes corresponding to the identified data points. In some instances, the concentrations of the one or more analytes in the sample are determined by interpolation of the known concentrations.

Some embodiments include an additional chemical sensing system. This chemical sensing system can include a plurality of sensors arranged on at least one substrate. A first sensor and a second sensor of the plurality of sensors can have different sensitivities to sense at least one analyte in a sample. Each of the plurality of sensors can be configured to output a signal in response to sensing the at least one analyte. The chemical sensing system can include a computer processor can be programmed to receive the signals output from the plurality of sensors. When the received signals and stored signals satisfy an update criterion, the computer processor can be programmed to update a first model and a second model. The first model can relate the signals output from the plurality of sensors to a feature representation. The second model can relate the feature representation to a latent representation. The computer processor can configure the chemical sensing system to determine concentrations of one or more analytes using the updated first model and the updated second model. In some embodiments, the update criterion can depend on a value of mutual information between the signals and the stored signals.

Some embodiments include a chemical sensing method. The chemical sensing method can include a set of operations. The operations can include receiving signals from a plurality of sensors of a chemical sensing system. The sensors can have different sensitivities to sense at least one analyte in the sample. Each of the sensors can be configured to output a signal in response to sensing the at least one analyte. The operations can include mapping the responses to an output representation having coordinate bases corresponding to analytes using a homeomorphic mapping. The operations can further include determining a concentration of a chemical in the sample from the output representation.

Some embodiments include a training method. The training method can include a set of operations. The operations can include receiving a training dataset generated by a plurality of sensors of a chemical sensing system. The sensors can have different sensitivities to sense at least one analyte in a sample. Each of the sensors can be configured to output a signal in response to sensing the at least one analyte. The operations can include generating a first model relating the signals output from the plurality of sensors to a feature representation using the training dataset. The operations can include generating a second model relating the feature representation to an output representation having coordinate bases corresponding to analytes using the training dataset. The operations can further include configuring a chemical sensing system to detect concentrations of the analytes using the first model and the second model.

Some embodiments include an additional chemical sensing system. This chemical sensor system can include a plurality of sensors arranged on at least one substrate. A first sensor and a second sensor of the plurality of sensors can have different sensitivities to sense at least one analyte in a sample. Each of the plurality of sensors can be configured to output a signal in response to sensing the at least one analyte. The chemical sensor system can include a computer processor programmed to perform a set of operations. The operations can include receiving the signals output from the plurality of sensors. The operations can further include determining a concentration of the at least one analyte in the sample. The concentration can be determined by providing the received signals as input to a first model trained to relate the signals output from the plurality of sensors to a feature representation to generate a feature representation output. The feature representation values can be provided to a second model trained to relate the feature representation to a latent representation, the latent representation having a lower dimensionality than the feature representation, to generate a latent representation output. The latent representation values can be provided to a third model trained to relate the latent representation to a straightened orthogonal representation to generate a straightened orthogonal representation output. One-dimensional manifolds in the straightened orthogonal representation corresponding to varying concentrations of a same analyte may have zero angle between them. One-dimensional manifolds in the straightened orthogonal representation corresponding to different analytes can be orthogonal. The straightened orthogonal representation values can be provided to a fourth model trained to relate the straightened orthogonal representation to an output representation having bases corresponding to analytes, the analytes including the at least one analyte, to generate an output representation output. The operations can include providing an indication of the determined concentration of the at least one analyte in the sample to a user.

Some embodiments include an additional chemical sensing system. The system can include at least one computer processor and at least one computer readable medium. The computer readable medium can contain instructions that, when executed by the at least one computer processor, can cause the chemical sensing system to perform a training process. The training process can include a set of operations. The operations can include receiving a training dataset generated by a plurality of sensors having different sensitivities to sense at least one analyte in a sample. Each of the plurality of sensors can be configured to output a signal in response to sensing the at least one analyte. The operations can include training a set of models using the training dataset. The training can include training a first model, a second model, a third model, and a fourth model. The first model can be trained to relate the signals output from the plurality of sensors to a feature representation. The second model can be trained to relate the feature representation to a latent representation, the latent representation having a lower dimensionality than the feature representation. The third model can be trained to relate the latent representation to a straightened orthogonal representation. One-dimensional manifolds in the straightened orthogonal representation corresponding to varying concentrations of a same analyte can have zero angle between them. One-dimensional manifolds in the straightened orthogonal representation corresponding to different analytes can be orthogonal. The fourth model can be trained to relate the straightened orthogonal representation to the output representation. The operations can further include configuring the chemical sensing system to detect concentrations of the analytes using the trained set of models relating the signals to the output representation.

Some embodiments are directed to a chemical sensing system, comprising: a plurality of sensors arranged on at least one substrate, wherein a first sensor and a second sensor of the plurality of sensors have different sensitivities to sense at least one analyte in a sample, each of the plurality of sensors being configured to output a signal in response to sensing the at least one analyte; and a computer processor programmed to: receive the signals output from the plurality of sensors; determine a concentration of the at least one analyte in the sample by: providing the received signals as input to a first model trained to relate the signals output from the plurality of sensors to a feature representation to generate feature representation values; providing the feature representation values as input to a second model trained to relate the feature representation to a latent representation to generate latent representation values, the latent representation having a lower dimensionality than the feature representation; providing the latent representation values as input to a third model trained to relate the latent representation to a straightened orthogonal representation to generate straightened orthogonal representation values, wherein: one-dimensional manifolds in the straightened orthogonal representation corresponding to varying concentrations of a same analyte have zero angle between them; and one-dimensional manifolds in the straightened orthogonal representation corresponding to different analytes are orthogonal;

providing the straightened orthogonal representation values as input to a fourth model trained to relate the straightened orthogonal representation to an output representation having bases corresponding to analytes, the analytes including the at least one analyte; and determining the concentration of the at least one analyte in the sample based on an output of the fourth model; and provide an indication of the determined concentration of the at least one analyte in the sample to a user.

Some embodiments are directed to a chemical sensing system, comprising: at least one computer processor; and at least one computer readable medium including instructions that, when executed by the at least one computer processor, cause the chemical sensing system to perform a training process, the training process comprising: receiving a training dataset including values associated with signals output from a plurality of sensors having different sensitivities to sense at least one analyte in a sample, each of the plurality of sensors configured to output the signal in response to sensing the at least one analyte; training a set of models using the training dataset by: training a first model to relate the signals output from the plurality of sensors to a feature representation; training a second model to relate the feature representation to a latent representation, the latent representation having a lower dimensionality than the feature representation; training a third model to relate the latent representation to a straightened orthogonal representation, wherein: one-dimensional manifolds in the straightened orthogonal representation corresponding to varying concentrations of a same analyte have zero angle between them; and one-dimensional manifolds in the straightened orthogonal representation corresponding to different analytes are orthogonal; and training a fourth model to relate the straightened orthogonal representation to the output representation having bases corresponding to analytes; and configuring the chemical sensing system to detect a concentration of the least one analyte in the sample using the trained set of models.

Some embodiments are directed to a chemical sensing method, comprising:

receiving, by a chemical sensing system, signals output from a plurality of sensors arranged on at least one substrate, wherein a first sensor and a second sensor of the plurality of sensors have different sensitivities to sense at least one analyte in a sample, each of the plurality of sensors being configured to output a signal in response to sensing the at least one analyte; determining, by the chemical sensing system, a concentration of the at least one analyte in the sample by: providing the received signals as input to a first model trained to relate the signals output from the plurality of sensors to a feature representation to generate feature representation values; providing the feature representation values as input to a second model trained to relate the feature representation to a latent representation to generate latent representation values, the latent representation having a lower dimensionality than the feature representation; providing the latent representation values as input to a third model trained to relate the latent representation to a straightened orthogonal representation to generate straightened orthogonal representation values, wherein: one-dimensional manifolds in the straightened orthogonal representation corresponding to varying concentrations of a same analyte have zero angle between them; and one-dimensional manifolds in the straightened orthogonal representation corresponding to different analytes are orthogonal; providing the straightened orthogonal representation values as input to a fourth model trained to relate the straightened orthogonal representation to an output representation having bases corresponding to analytes, the analytes including the at least one analyte; and determining the concentration of the at least one analyte in the sample based on an output of the fourth model; and provide, by the chemical sensing system, an indication of the determined concentration of the at least one analyte in the sample to a user.

Some embodiments are directed to a computer-implemented training method, comprising: receiving a training dataset including values associated with signals output from a plurality of sensors having different sensitivities to sense at least one analyte in a sample, each of the plurality of sensors configured to output the signal in response to sensing the at least one analyte; training, using at least one computer processor, a set of models using the training dataset by: training a first model to relate the signals output from the plurality of sensors to a feature representation; training a second model to relate the feature representation to a latent representation, the latent representation having a lower dimensionality than the feature representation; training a third model to relate the latent representation to a straightened orthogonal representation, wherein: one-dimensional manifolds in the straightened orthogonal representation corresponding to varying concentrations of a same analyte have zero angle between them; and one-dimensional manifolds in the straightened orthogonal representation corresponding to different analytes are orthogonal; and training a fourth model to relate the straightened orthogonal representation to the output representation having bases corresponding to analytes; and configuring a chemical sensing system to detect a concentration of the least one analyte in the sample using the trained set of models.

The foregoing summary is provided by way of illustration and is not intended to be limiting. It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Some conventional chemical sensing systems are based on lock-and-key sensors responsive to only one chemical or are based on gas chromatography-mass spectrometry techniques that require equipment that is bulky and prohibitively expensive for many applications and are incapable of detecting chemicals in the environment in near real-time. The inventors have recognized and appreciated that conventional chemical sensing systems may be improved by providing a system that mitigates, at least in part, at least some of the limitations described above.

Chemical sensors are physical devices that exhibit a measurable response to the presence of one or more chemical species. In a chemical sensor array, multiple chemical sensors are operated in the context of the same sensing application. In the description that follows, chemical sensors are referred to as sensors and chemical sensor arrays are referred to as sensor arrays.

A sensor can be operated in an environment that includes one or more chemical species. At least one of the chemical species in the environment may be present in a liquid phase and/or a gas phase. The concentration of the chemical species in the environment may be quantified as a scalar value in conjunction with a chosen unit of measurement. For example, the concentration of gaseous methane in air can be quantified in terms of molar concentration.

A sensor can be configured to sense a concentration of one or more relevant chemical species (referred to herein as analytes) in the environment. The concentration of analytes in the environment is referred to herein as the composition of the environment. For example, a carbon monoxide detector can be configured to sense a concentration of carbon monoxide present in an environment also including other chemical species (e.g., oxygen and nitrogen). When a sensor array is configured to detect M analytes, a unit of measurement defines an M-dimensional vector space V isomorphic to $R^M$. The elements $\vec{v} \in V$ each uniquely describe a composition of the environment. The composition of the environment $\vec{v}$ as measured by a sensor may depend on a location of the sensor and may vary over time.

Figure 1A:
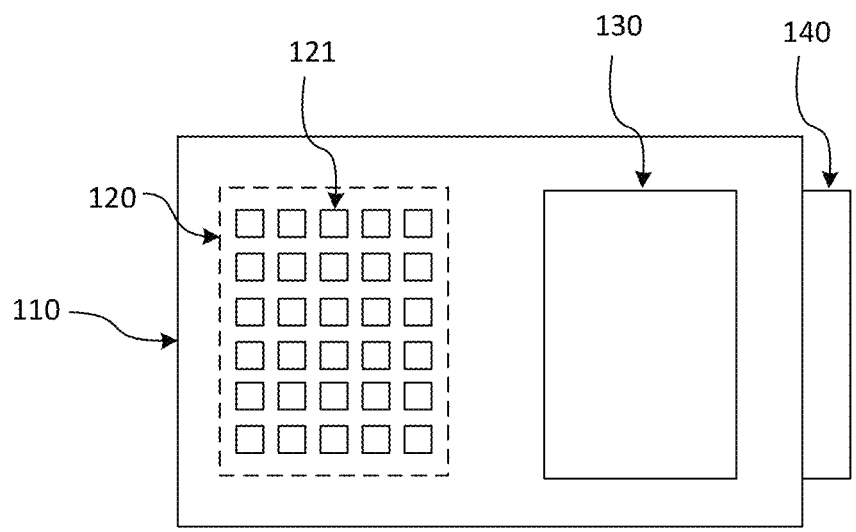
FIGS. 1A and 1B depict views of an exemplary component of a chemical sensing system.
Figure 1B:
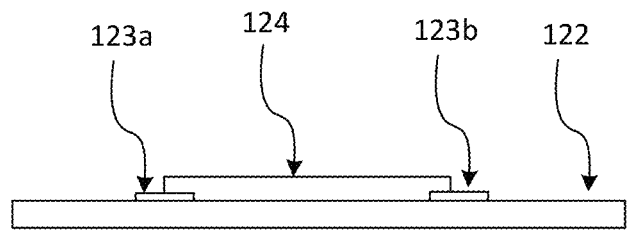

FIGS. 1A and 1B depict views of an exemplary chemical sensing system 100. Chemical sensing system 100 includes a sensor array 120. Individual sensor outputs from a plurality of sensors in the array may exhibit incomplete information about the chemical species in the environment in which the chemical sensing system is placed. For example, each sensor output may exhibit a dependence on multiple, time varying extraneous variables (e.g., temperature, humidity, etc.) that are not well specified based on the output of that sensor alone. By including multiple sensors in an array, the chemical sensing system may be configured to estimate the chemical composition of an environment using multiple output signals generated by the multiple sensors in the array. As described in more detail below, some embodiments process the output from multiple sensors in an array using an inferential model to generate an estimate of a concentration of one or more chemical species in the environment.

Chemical sensing system 100 includes a base 110 configured to support a sensor array 120. Base 110 may be implemented using any suitable substrate including, but not limited to, a circuit board. The sensor array 120 includes a plurality of sensors (e.g., sensor 121). The sensors may be arranged in rows and columns, as shown, or the sensors may be arranged in another arrangement (e.g., concentric circles, staggered rows, etc.). The described location and orientation of the sensors on chemical sensing system 100 are not intended to be limiting.

Chemical sensing system 100 includes a controller 130. In some embodiments, controller 130 is configured to provide power to the plurality of sensors. In some embodiments, controller 130 is configured to acquire signals from the plurality of sensors. For example, each of the sensors may include, or be a part of, a Wheatstone bridge or another circuit configured to measure changes in resistance. Controller 130 may be configured to provide power for the sensors and/or acquire signals from the sensors corresponding to changes in resistance measured by the sensors. In some embodiments, controller 130 is further configured to provide one or more of signal conditioning, signal processing, and signal communication. For example, controller 130 may be configured to filter and amplify signals received from the sensors. In some embodiments, controller 130 is further configured to perform at least some of the mapping operations described in more detail below. For example, controller 130 may be configured to implement one or more models relating the signals output by the sensors to a latent representation, or to an output representation having one or more axes corresponding to relevant analytes. In some embodiments, controller 130 includes at least one storage device (e.g., a memory) configured to store parameters that define one or more of the mapping operations, described in more detail below.

Chemical sensing system 100 includes a communications component 140, which can include hardware and/or software configured to enable chemical sensing system 100 to communicate with the chemical sensing system (or other devices). For example, communications component 140 may include a network controller configured to provide local area network connectivity, a port controller configured to provide parallel port and/or serial port connectivity, and/or a wireless controller configured to provide WIFI, BLUETOOTH, ZIGBEE or similar connectivity.

In accordance with some embodiments, a sensor (e.g., sensor 121) includes a substrate 122 and one or more electrodes (e.g., electrodes 123a and 123b) disposed on substrate 122. In one implementation of sensor 121, a conductive thin film 124 is disposed on and between electrodes 123a and electrodes 123b as shown. For example, thin film 124 can include conductive nanoparticles. In some embodiments, thin film 124 is chemically sensitive. For example, thin film 124 may undergo a physical change (e.g., swelling, contracting, and/or a change in composition or state) upon exposure to an analyte. The physical change in the thin film 124 may result in a change in resistance between electrode 123a and electrode 123b. Controller 130 may be configured to monitor the resistance between electrode 123a and electrode 123b, resulting in an output signal from the sensor that is detectable by controller 130. The output signal may include semantic information concerning one or more analytes introduced to the sensor.

In some embodiments, one or more of the sensors in sensor array 120 are configured with differing sensitivities to different analytes. For example, thin films for different sensors in the array may be configured to provide different degrees of physical change in response to exposure to the same analyte. As an additional example, a thin film for a sensor can be configured to provide different degrees of physical change in response to exposure to different analytes. Accordingly, in some embodiments, the output signals from different sensors in the array may differ in the presence of the same analyte and/or the output signal from the same sensor may differ in the presence of different analytes in the environment. These differences may include, but are not limited to, differences in amplitude and/or temporal characteristics of the output signal.

Figure 2A:
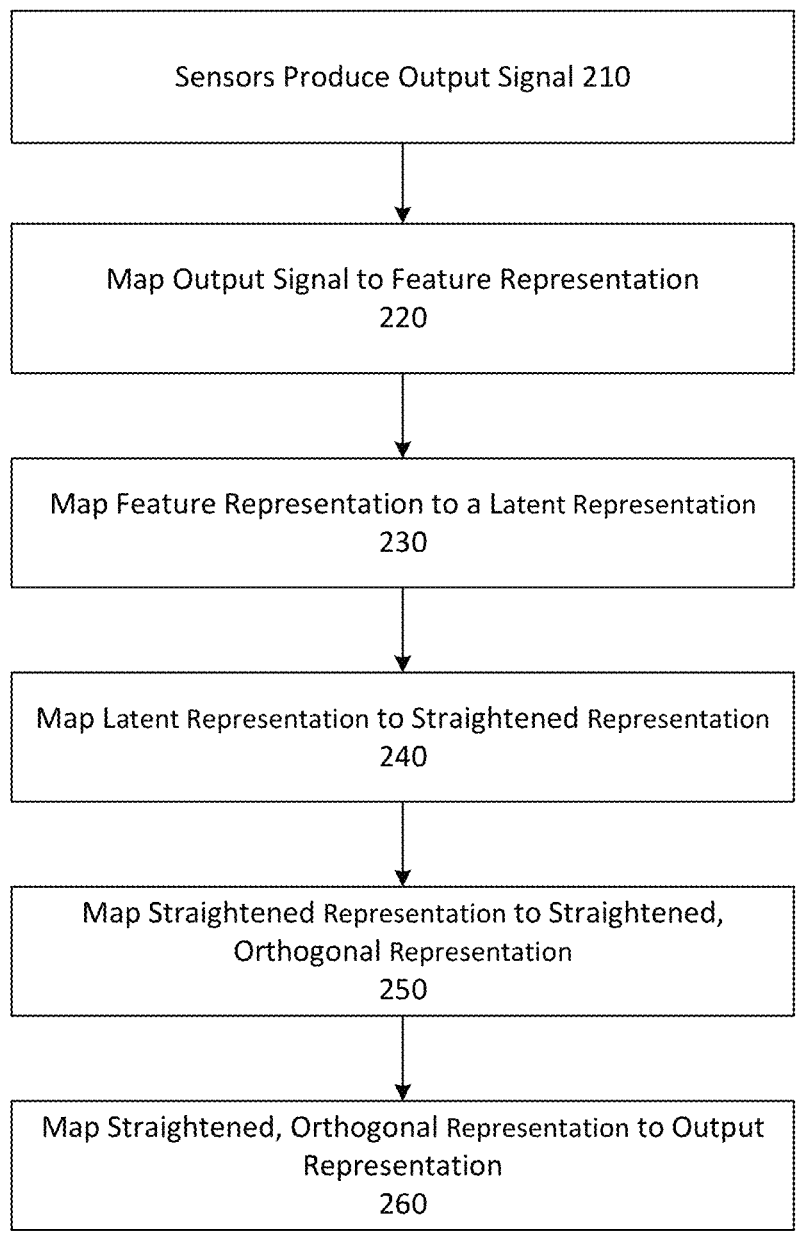
FIG. 2A depicts a sequence of exemplary mappings from signals output by sensors to an output representation having bases corresponding to relevant analytes.
Figure 2B:
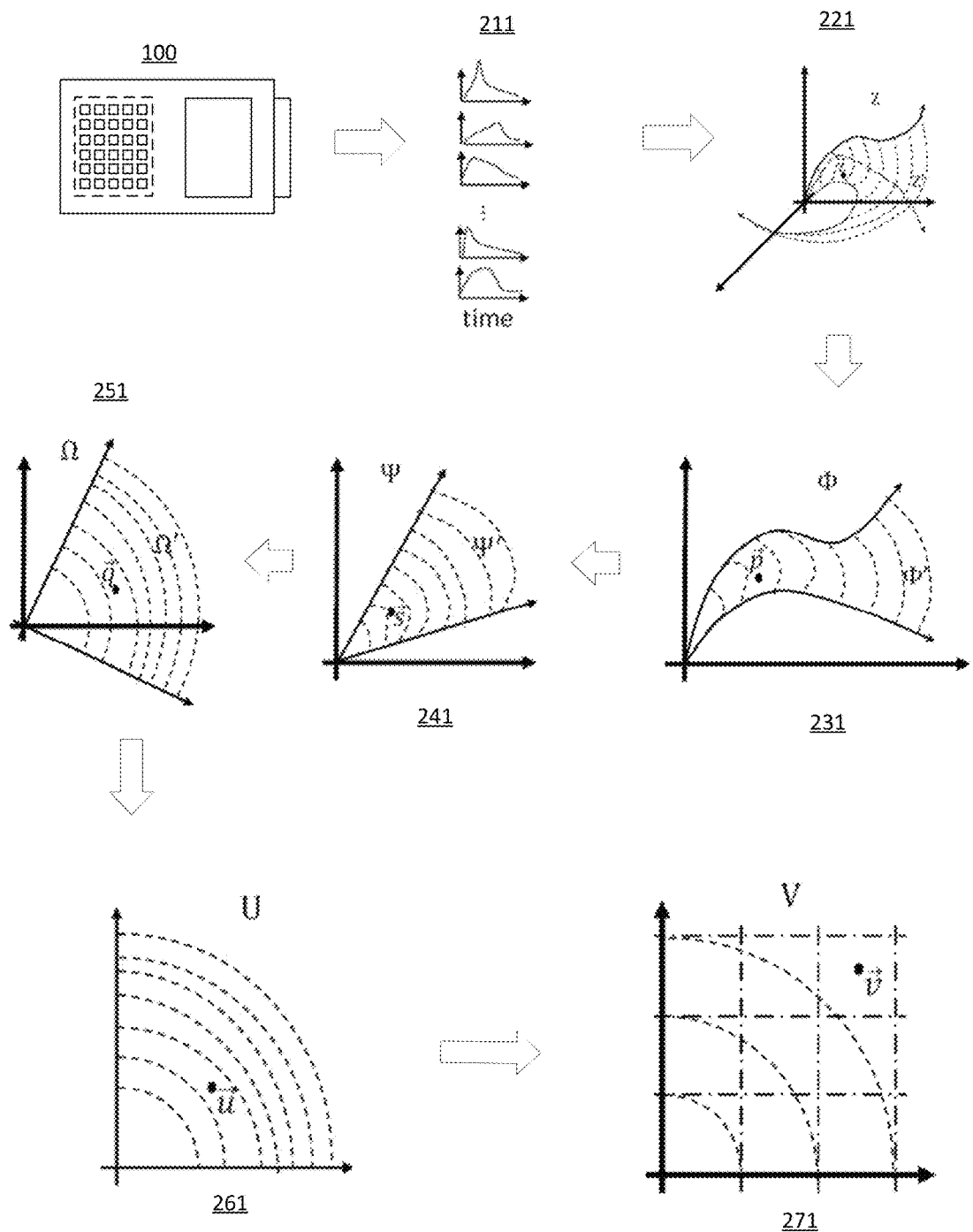
FIG. 2B depicts a sequence of exemplary representations corresponding to the mappings of FIG. 2A.

FIG. 2A depicts an exemplary process 200 of mapping signals output by sensors (e.g., the sensors of chemical sensing system 100) to an output representation having bases corresponding to relevant analytes (e.g., the vector space V, described above). FIG. 2B depicts a sequence of exemplary representations (also referred to herein as models or sub-models) corresponding to the mappings of FIG. 2A. Process 200 can operate on input data (e.g., datasets, streaming data, files, or the like) divided into semantically separate partitions corresponding to different environmental and operational contexts. For example, the input data may be divided into multiple datasets, data streams, files, etc. corresponding to different sensors, times, contexts, environments, or the like. Such partitions may contain multiple input data entries, one input data entry, or no input data entries. Under such partitioning, the datasets and data streams may be viewed as composites of the individual semantic partitions, and the analyses applied to the datasets and data streams may be equivalently applied to semantic partitions and vice-versa.

The input data may include output signals obtained from sensors (e.g., raw data output from the sensors) and/or data derived from the signals output from the sensors (e.g., one or more features extracted from the output signals). In some aspects, the output signals obtained from the sensors may be filtered to reduce noise in the output signals. Any suitable filtering technique may be used depending on the nature of the sensor response and the noise present in the output signals. Unless otherwise specified, the output signals described herein may be either filtered output signals or non-filtered output signals. In some embodiments, the input data includes time values. For example, the input data may include timestamps corresponding to output signal values. In some embodiments, time values may be implicitly determined from the data. For example, the input data may include an initial timestamp and a sampling frequency such that time values for input data following the initial timestamp may be determined based on the initial timestamp and the sampling frequency.

In some embodiments, the input data can include concentration information corresponding to the output signals. When the input data lacks concentration information for all of the relevant analytes, the input data is referred to herein as "unlabeled data." When the input data lacks concentration information for some of the relevant analytes, the input data is referred to herein "partially labeled data." When the input data includes concentration information for all of the relevant analytes, the input data is referred to herein as "labeled data." In some embodiments, the input data includes contextual information. The contextual information may include, for example, information about the environment of the device such as the temperature of the environment, the application the system is employed in, explicit information about the presence or absence of irrelevant analytes, or other contextual information relating to the operation of the sensor array.

In some embodiments, process 200 is implemented by sequentially applying one or more models to the data. The one or more models may include parameters and hyperparameters stored in a memory component of the chemical sensing system. In some embodiments, the parameters are learned using machine learning techniques, examples of which are described in more detail below. A chemical sensing system configured to apply the sequence of one or more models according to the learned parameters and hyperparameters to output signals may infer a chemical composition of an environment from the output signals.

A sequence of models that collectively map the input data to the output representation (e.g., the vector space V, described above) may be generated in place of a single model that performs the same function. Using a sequence of models may improve the flexibility of the chemical sensing system. Furthermore, the effect of each individual model may be more easily reviewed and/or interpreted when using a sequence of models that collectively map the input data to the output representation, allowing for convenient adjustment or debugging of individual models.

In some embodiments, the sequence of models may include a first model that relates the output signals to an intermediate representation (e.g., a feature representation, latent representation, or straightened orthogonal representation, as described herein) and a second model that relates the intermediate representation to the output representation. Different versions of the first model may be specific to different implementations or instances of chemical sensing system 100. Similarly, different versions of the second model may relate the intermediate representation to different output representations. Depending on the chemical sensing system and the desired output representation, an appropriate version of the first model may be used together with the appropriate version of the second model. The two models may be generated separately (e.g., at different times or locations, or by different devices), or applied separately. As one example, a first chemical sensing system can apply the first model to the output signals to generate the intermediate representation. A second chemical sensing system can subsequently apply the second model to the intermediate representation to generate the output representation. In some embodiments, the first model can be specific to the first device. Thus, a first device-specific model can be trained to map input data acquired by the first device to the intermediate representation. The first device-specific model can subsequently be used to specify initial parameters for training additional device-specific models. For example, when training a second device-specific model for a second device, at least some of the parameters of the second device-specific model can be initialized to at least some of the parameters of the first device-specific model. In some embodiments, the second model can be trained independent of any particular device. For example, when the second model is implemented as a device-independent model, it can be trained to map input data from intermediate representations generated by one or more device-specific models to the output representation.

In some embodiments, one or both of first and second models includes at least two sub-models, each of which divides the mapping for a model into multiple sub-mappings which may undergo a separate learning process. For example, in some embodiments, the second model is divided into a first sub-model relating the feature representation output from the first model to a latent representation, a second sub-model relating a latent representation to a straightened orthogonal representation, and a third sub-model relating a straightened orthogonal representation to the output representation.

The composition and training of the models and/or submodels used in accordance with some embodiments, are described in more detail below. In some embodiments, one or more of the models or sub-models are trained using parametric techniques, such as support vector machines, random forests or deep neural networks. In other embodiments, one or more of the models or sub-models are trained using non-parametric techniques, such as t-distributed stochastic neighbor embedding (t-SNE) or k-nearest neighbors techniques (k-NN).

For convenience, FIGS. 2A and 2B are described with regard to tuples of the form $\{D(t_i)=(t_i, C(t_i), \vec{x}(t_i), \vec{a}(t_i))\}$, where $t_i$ is a unique timestamp, $\vec{x}(t)=\langle x_1(t), \ldots, x_N(t)\rangle$ is the response of a sensor array including N sensors at time $t_i$, and $\vec{a}(t_i)$ may be the corresponding vector of concentrations of relevant analytes. As described above, $\vec{x}(t)$ may represent a filtered version of the output signals from the sensors to reduce noise in the output signals. When information about the concentration of a relevant analyte is not available, the corresponding elements of $\vec{a}(t_i)$ may include an element (a "null element") indicating the unavailability of such information (e.g., a default value, a NaN, or the like). For example, when no information about the concentration of relevant analytes is available, $\vec{a}(t_i)$ may be a vector of null elements. As used herein, a data entry $D(t_i)$ is referred to as "unlabeled" when all elements of $\vec{a}(t_i)$ are null elements, partially labelled when some but not all elements of $\vec{a}(t_i)$ are null elements, and $D(t_i)$ is referred to as "labelled" when none of the elements of $\vec{a}(t_i)$ are null elements. $C(t_i)$ may include a vector of contextual information, such as the contextual information described above. However, the disclosed embodiments are not limited to tuples of the form $\{D(t_i)=(t_i, C(t_i), \vec{x}(t_i), \vec{a}(t_i))\}$.

In operation 210, sensors (e.g., sensors in sensor array 120) of a sensing device (e.g., chemical sensing system 100) may transduce a chemical signal $\vec{v}$ dependent on the composition of the environment into electrical output signals $\vec{x}(t)$ (e.g., from chemical sensing system 100 to output signals 211, as depicted in FIG. 2B). In some embodiments, the values of output signals 211 may reflect changes in the composition of the environment over time. In some embodiments, these output signals may include transient changes in value in response to a change in the composition of the environment. For example, a baseline value prior to the change in the composition of the environment may be approximately the same as a steady-state value reached after the change in the composition of the environment. In various embodiments, these output signals may reach a new steady-state value dependent on the changed composition of the environment.

In operation 220, the output signals are applied to a model that relates output signals to a feature representation (e.g., a mapping from output signals 211 to feature representation 221, as depicted in FIG. 2B) to generate feature vectors corresponding to the output signals. In this manner, the model may de-convolve relevant information from the output signals. The relationship established by the model can be expressed, for an output signal $x_i(t)$, as a map to a feature representation, $\zeta_i: \mathbb{R}^{T_i} \to \mathbb{R}^{K_i}$, where $T_i$ denotes some (possibly infinitely large) number of samples that span some time interval $[t_1, t_{T_i}]$, and $K_i$ denotes a number of features extracted from the output signal. Such a map produces a feature vector $\vec{z}_j = \zeta_i(x_i([t_1, t_{T_i}]))$, where $\vec{z}_j \in \mathbb{R}^{K_i}$. As discussed herein, may be expressed as a parametric function of some parameter set $\theta_i$: $\vec{z}_j = \zeta_i(x_i([t_1, t_{T_i}]); \theta_i)$. Values for these parameters may be estimated using, for example, machine learning techniques such as feedforward neural networks and Gaussian processes.

In some embodiments, the number of maps may not equal the number of output signals $x_i(t)$. For example, features may not be extracted from some output signals (resulting in fewer maps), or features may be extracted from combinations of output signals in addition to individual output signals (resulting in additional maps). In general, when the number of output signals is N, the number of maps $\zeta_i$ will be equal to N'. The result of applying $\zeta=\{\zeta_1, \ldots, \zeta_{N'}\}$ to $\vec{x}(t)$ may be expressed as a composite feature vector $\vec{z}=(z_1, \ldots, z_{N'})$, where $\vec{z} \in \mathbb{R}^K$, and $$K = \sum_i K_i$$

is the collection of features extracted from all maps comprising $\zeta$. As used herein, such a composite feature vector is referred to as a feature vector. For $\vec{z}$ as defined above, let the span of all possible feature vectors $\vec{z}$ be denoted as the feature space Z, where $Z \subseteq \mathbb{R}^K$.

In some embodiments, N may be a large number, and K may be larger than N. As such, numerical methods applied in Z may suffer from the curse of dimensionality. Furthermore, a change in concentration $\Delta \vec{v}$ may yield a non-linear change $\Delta \vec{z}$ in the feature vector, which may, in some cases, preclude the use of linear dimensionality reduction techniques.

In some embodiments, properties of the feature space Z may be used to associate feature vectors with analytes, without relying on vectors of concentrations of relevant analytes (e.g., without relying on $\vec{a}(t_i)$). These associations may be used to train models that implement mappings imposing straightness and orthogonality conditions on the data. For example, an association can be created between feature vectors corresponding to varying concentrations of the same analyte. A model can be generated, using this association, that implements a mapping to a representation in which points corresponding to the feature vectors are aligned along a single vector. As an additional example, a first association can be created between first feature vectors corresponding to varying concentrations of a first analyte and a second association can be created between second feature vectors corresponding to varying concentrations of a second analyte. A model can be generated, using the first and second associations, that implements a mapping to a representation in which first points corresponding to the first feature vectors are aligned along a first vector, second points corresponding to the second feature vectors are aligned along a second vector, and the first vector and second vector are orthogonal.

In some embodiments, an iterative process is used to identify feature vectors corresponding to varying concentrations of a single analyte. This process can be performed automatically (e.g., without user direction or input). This approach assumes that feature vectors corresponding to varying concentrations of a single analyte are on the outside, or hull, of manifold Z'. Points in Z' corresponding to combinations of two or more analytes may lie between these exterior points, either on the hull of manifold Z' or in the interior of manifold Z'. A sequence of samples including a fixed concentration of a first analyte and decreasing concentrations of a second analyte approach a location in Z' corresponding to the fixed concentration of a first analyte along a first trajectory. A sequence of samples including the fixed concentration of the first analyte and decreasing concentrations of a third analyte approach the location in Z' corresponding to the fixed concentration of the first analyte along a second trajectory, distinct from the first trajectory. Thus, points corresponding to varying concentrations of a single analyte can be identified as points on the hull of manifold Z' where trajectories defined by neighboring points change (e.g., locations with local gradient changes). The following iterative process may be used to identify such points.

As a first step, a space D is initialized to equal space Z and includes all of the points in space Z. A point $z_1$ in D is selected. Another point $z_2$ in a neighborhood of $z_1$ is selected and a vector $\vec{z_1 z_2}$ created. A sequence of points is then identified, each point in the sequence in a neighborhood of the preceding point in the sequence satisfying a directionality criterion with respect to $\vec{z_1 z_2}$. Satisfaction of this directionality criterion may indicate that a point is sufficiently aligned with the vector $\vec{z_1 z_2}$. In some embodiments, the directionality criterion may depend on a vector between the preceding point in the sequence and the current point in the sequence. For example, the directionality criterion may depend on a cosine value of the angle between $\vec{z_1 z_2}$ and the vector. When the cosine value is less than a threshold, the directionality criterion may not be satisfied. For example, a first point $z_3$ in the sequence may be in a neighborhood of $z_2$ and may satisfy the directionality criterion when a cosine value of the angle between $\vec{z_1 z_2}$ and $\vec{z_1 z_3}$ is greater than a threshold. In various embodiments, the directionality criterion may depend on a distance from the next point in the sequence to a projection of the vector $\vec{z_1 z_2}$. The sequence may end when no further point can be identified along this direction. Additional sequences can be generated in this fashion for all points $z_1$ in Z and $z_2$ in the neighborhood of $z_1$. The set of final points E for all of the sequences may then define a boundary space in D. The space D can be updated to include only the boundary points E. The process of identifying boundary points can then be repeated to generate a new set of final points E.

This process can be repeated until E comprises a set of one-dimensional manifolds that cross an origin corresponding to an absence of a sensor response. Each of these one-dimensional manifolds comprises feature vectors corresponding to pure chemicals or base analytes. By applying this process, feature vectors can be associated with one-dimensional manifolds correspondent to the base analytes. This association can then be used to perform unsupervised learning in operations 241 and 251, without relying on labels for the samples. In semi-supervised techniques, partial availability of labels indicating concentrations associated with feature vectors can help validate the formation of each map and space by comparing a label for a sample with a position corresponding to the sample in each space. Partial labels can also be used to label an axis corresponding to base analytes. For example, when a sample lies on or near an axis and a label for the sample indicates concentrations of analytes, the axis can be labeled as corresponding to the analyte having the greatest concentration.

In some embodiments, $\vec{x}(t)$ may be continuous with respect to changes in $\vec{v}(t)$. Mapping $\zeta$ may be selected so as to preserve the continuity of $\Delta \vec{z}(t)$ with respect to $\Delta \vec{v}(t)$. When the output signal $\vec{x}(t)$ is unique for each chemical composition of the environment $\vec{v}(t)$, and $\zeta$ is selected to preserve uniqueness of $\vec{z}$ with respect to $\vec{v}$, then there exists a one-to-one mapping $H^{-1}$ between the exemplary output representation V and Z' where the image V defines a continuous manifold $Z' \subseteq Z$ as depicted in FIG. 2B.

When exemplary output representation V and Z' are open sets, the one-to-one mapping $H^{-1}$ is a homeomorphism. By definition, a homeomorphism H then exists between Z' and V. In such instances, Z' comprises a manifold of dimension M embedded in Z (as depicted in feature space 221 of FIG. 2B). Furthermore, each dimension of V maps to a one-dimensional, potentially non-linear manifold embedded in Z'. The mapping $\Omega$ from Z' and V may thus be decomposed into sub-mappings. As described above, sub-models may implement these sub-mappings. Such sub-models may be easier to generate than a model that implements H, and may provide additional flexibility to the chemical sensing system.

In operation 230, the feature vectors generated in operation 220 can be applied to a first sub-model that relates the feature representation Z to a latent representation $\Phi$ (e.g., from feature representation 221 to latent representation 231, as depicted in FIG. 2B) to generate latent value vectors corresponding to the feature vectors. In some embodiments, the latent representation $\Phi$ can be an inner product space. The latent representation $\Phi$ can be of the same dimension as the manifold Z'. As a non-limiting example, when Z' is a plane embedded in Z, then the latent representation $\Phi$ may be a two-dimensional space (e.g., latent representation 231, as depicted in FIG. 2B). The first sub-model may implement a mapping $\varphi: Z \to \Phi$. Such a map may produce a latent value vector $\vec{p} = \varphi(\vec{z})$, where $\vec{p} \in \mathbb{R}^{dim(Z')}$. In some embodiments, when Z' is not embedded in Z, $\varphi$ may reduce to the identity function. As discussed herein, $\varphi$ may be expressed as a parametric function of some parameter set $\Lambda$: $\vec{p} = \varphi(\vec{z}; \Lambda)$. Values for parameter set $\Lambda$ may be estimated using machine learning techniques such as feedforward neural networks and Gaussian processes. In some embodiments, the mapping $\varphi: Z \to \Phi$ fulfills the following conditions: $\varphi$ is a continuous mapping between Z' and $\Phi$, $\varphi$ is bijective from Z' to $\Phi$, $\varphi^{-1}$ is a continuous mapping between $\Phi$ and Z', and $\varphi^{-1}$ is bijective from $\Phi$ and Z'. The above conditions may follow from the homeomorphism between Z' and $\Phi$.

In operations 240 and 250, the latent value vectors generated in operation 230 can be applied to a second sub-model that relates the latent representation $\Phi$ to a straightened, orthogonalized representation $\Omega$. In some embodiments, this second sub-model includes two component models. As described above, multiple component models may provide more flexibility and be more easily interpreted than a single model providing the same functionality.

In operation 240, the latent value vectors generated in operation 230 can be applied to the first component model to generate aligned vectors corresponding to the latent value vectors (e.g., from latent representation 231 to straightened representation 241, as depicted in FIG. 2B). The first component model may relate latent representation $\Phi$ to straightened representation $\Psi$. In latent representation $\Phi$, samples including varying concentrations of a single analyte may be described by a non-linear, one-dimensional manifold. The first component model may implement a mapping $\psi: \Phi \to \Psi$ that maps each such manifold to a straightened non-linear, one-dimensional manifold in $\Psi$. For example, two differing concentrations of the same analyte (e.g., $\vec{v_2} = c\vec{v_1}$, $\vec{v_1}, \vec{v_2} \in V$, $c \in \mathbb{R}$) may map to two latent value vectors (e.g., $\vec{p_1}, \vec{p_2} \in \Phi$). Mapping $\psi$ may map $\vec{p_1}$ and $\vec{p_2}$ to $\vec{s_1}, \vec{s_2} \in \Psi$ such that an angle between $\vec{s_1}$ and $\vec{s_2}$ is minimized. For example, $\psi$ may be determined such that cosine distance $d(\vec{s_1}, \vec{s_2})$ is maximized. When the manifolds in $\Phi$ are already straight, $\psi$ may reduce to the identity function. As discussed herein, $\psi$ may be expressed as a parametric function of some parameter set $\Sigma$: $\vec{s} = \psi(\vec{p}; \Sigma)$. Values for parameter set $\Sigma$ may be estimated using machine learning techniques, such as feedforward neural networks and Gaussian processes. In some embodiments, the mapping $\psi$: $\Phi \rightarrow \Psi$ fulfills the following conditions: $\psi$ is a continuous mapping between $\Phi$ and $\Psi$, $\psi$ is bijective from $\Phi$ to $\Psi$, $\psi^{-1}$ is a continuous mapping between $\Psi$ and $\Phi$, and $\psi^{-1}$ is bijective from $\Psi$ to $\Phi$. The above conditions may follow from the homeomorphism between $\Psi$ and $\Phi$. Furthermore, function $\psi$ may reduce the impact of noisy data, as $\psi$ may align latent value vectors in $\Phi$ corresponding to noisy measurements of the same analyte along the same direction in $\Psi$.

In operation 250, the latent value vectors generated in operation 230 can be applied to the second component model to generate independent vectors corresponding to the aligned vectors (e.g., from straightened representation 241 to orthogonal, straightened representation 251, as depicted in FIG. 2B). The second component model may relate straightened representation $\Psi$ to straightened, orthogonal representation $\Omega$. In straightened representation $\Psi$, varying concentrations of the same analyte may map to a straightened, non-linear, one-dimensional manifold (e.g., straightened representation 241, as depicted in FIG. 2B). The second component model may implement a mapping $\omega$: $\Psi \rightarrow \Omega$ that maps such manifolds to orthogonal, straightened non-linear, one-dimensional manifolds in $\Psi$. For example, two samples of two different analytes (e.g., $\vec{v}_2 \perp \vec{v}_1$, $\vec{v}_1, \vec{v}_2 \in V$) may map to two independent vectors (e.g., $\vec{s}_1, \vec{s}_2 \in \Psi$). Mapping $\omega$ may map $\vec{s}_1$ and $\vec{s}_2$ to $\vec{q}_1, \vec{q}_2 \in \Omega$ such that an angle between $\vec{q}_1$ and $\vec{q}_2$ is maximized. For example, $\Omega$ may be determined such that cosine distance $d(\vec{q}_1, \vec{q}_2)$ is minimized. When the manifolds corresponding to the different analytes in $\Psi$ are already orthogonal, $\omega$ may reduce to the identity function. As discussed herein, $\omega$ may be expressed as a parametric function of some parameter set Y: $\vec{q} = \omega(\vec{s}; Y)$. Values for parameter set Y may be estimated using machine learning techniques, such as feedforward neural networks and Gaussian processes. In some embodiments, the mapping $\omega$: $\Psi \rightarrow \Omega$ fulfills the following conditions: $\omega$ is a continuous mapping between $\Psi$ and $\Omega$, $\omega$ is bijective from $\Phi$ to $\Omega$, $\omega^{-1}$ is a continuous mapping between $\Omega$ and $\Psi$, and $\omega^{-1}$ is bijective from $\Omega$ to $\Psi$. The above conditions may follow from the homeomorphism between $\Omega$ and $\Psi$. Furthermore, function $\omega$ may reduce the impact of noisy data, as $\omega$ may map aligned vectors in $\Omega$ corresponding to noisy measurements of different analyte along orthogonal directions in $\Psi$.

In operations 260 and 270, the independent, aligned vectors generated in operation 250 can be applied to a third sub-model that relates the orthogonal, straightened representation $\Omega$ to the output representation V. In some embodiments, this third sub-model can include two component models. As described above, multiple component models may provide more flexibility and be easier to train than a single model providing the same functionality.

In operation 260, the first component model can be configured to align the orthogonal, straightened manifolds corresponding to varying concentrations of differing analytes with the standard basis vectors of $\mathbb{R}^M$ (e.g., from orthogonal, straightened representation 251 to standard basis representation 261, as depicted in FIG. 2B). For example, the first component model can be configured to implement a mapping $\tau$: $\Omega \rightarrow U$ that maps manifolds corresponding to varying concentrations of a single base analyte to the standard basis vectors $e_i$ of $\mathbb{R}^M$. For example, when the chemical sensing system is configured to detect two analytes, samples including varying concentrations of a first analyte can lie on a first one-dimensional, straightened manifold in $\Omega$. Samples including varying concentrations of the second analyte can lie on a second one-dimensional, straightened manifold in $\Omega$, orthogonal to the first one-dimensional, straightened manifold. In this two-dimensional example, the first component model can map the first one-dimensional, straightened manifold to the standard basis vector $e_1 = [1 \ 0]$ and map the second one-dimensional, straightened manifold to the standard basis vector $e_2 = [0 \ 1]$. When the chemical system is configured to detect additional relevant analytes, the representation $\Omega$ will contain more manifolds corresponding to these additional relevant analytes, which will be mapped to additional standard basis vectors $e_i$ of $\mathbb{R}^M$. As discussed herein, r may be expressed as a parametric function of some parameter set $\Pi$: $\vec{u} = \tau(\vec{q}; \Pi)$. Values for parameter set $\Pi$ may be estimated using machine learning techniques, such as feedforward neural networks and Gaussian processes. In some embodiments, $\tau$ may comprise one or more rotation matrices. The parameters comprising parameter set $\Pi$ may be values in the one or more rotation matrices.

In operation 270, the second component model can be configured to map from the manifolds corresponding to single analytes in U to linearized manifolds corresponding to single analytes in V (e.g., from standard basis representation 261 to output representation 271, as depicted in FIG. 2B). In some embodiments, for example, doubling a concentration of an analyte in the environment may not result in a doubling of a corresponding value in U. Accordingly, the first component model can be configured to implement a mapping $\eta$: $U \rightarrow V$ that maps the standard basis representation U to output representation V. The relationship between concentrations of analytes in the environment and values in output representation V may be linear. For example, a doubling of a concentration of an analyte in the environment may result in a doubling of a corresponding value in V. As discussed herein, $\eta$ may be expressed as a parametric function of some parameter set $\Gamma$: $\vec{v} = \eta(\vec{u}; \Gamma)$. Values for parameter set $\Gamma$ may be estimated using machine learning methods, such as feedforward neural networks and Gaussian processes.

The above described process 200 is intended to be exemplary and non-limiting. In some embodiments, one or more acts of process 200 may be omitted. For example, act 230 may be omitted when the Z' is not embedded in Z. As an additional example, acts 240 and 250 may be omitted when the one-dimensional manifolds corresponding to the varying concentrations of single analytes do not require straightening or orthogonalization. Furthermore, the association of one-dimensional manifolds in $\Omega$ with analytes and the generation of output representation V can be combined into a single act. In this single act, each element of V may be described by a unique directional vector $\hat{s}_k$ in $\Psi$. The collection of M vectors $\hat{s}_k$ may define a basis for $\Psi$. This basis may be orthogonalized and transformed to the standard basis of $\mathbb{R}^M$ using, standard linear algebra techniques, and described by the linear transformation $\vec{u} = G\vec{s}$. This linear transformation may be more generally denoted as a parametric function of G: $\vec{u} = \rho(\vec{s}, G)$. In the case where the vectors $\hat{s}_k$ already form an orthogonal basis, G reduces to the identity function. Under the linear transformation G, the vector $\hat{u}_k = G\hat{s}_k$ becomes a scalar multiple of a standard basis vector $\hat{e}_k$, and $\vec{v}$ may be recovered by a mapping $\eta_2$: $U \rightarrow V$ that maps to output representation V. As discussed herein, $\eta_2$ may be expressed as a parametric function of some parameter set Γ: $\vec{v}=\eta_2(\vec{u}; \Gamma)$. Values for parameter set Γ may be estimated using machine learning techniques, such as feed-forward neural networks and Gaussian processes. In this example, in contrast to the example provided above with respect to acts 240 and 250, labels identifying the samples in $\vec{u}$ corresponding to the axes in V may be required to generate G and $\eta_2$.

FIGS. 3A to 3G depict an example of domain transfer between two instances of a chemical sensing system in accordance with some embodiments. For example, the first instance of the chemical sensing system (depicted in FIG. 3A) may gather input data using a first instance of chemical sensing system 100 and the second instance of the chemical sensing system (depicted in FIG. 3B) may gather input data using a second instance of chemical sensing system 100. These two instances of chemical sensing system 100 may differ due to normal manufacturing variations, or may include differing types of chemical sensor or differing models or versions of the same type of chemical sensor.

Figure 3A:
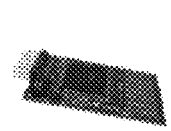
FIGS. 3A to 3G depict an example of domain transfer between two instances of a chemical sensing system.
Figure 3C:
Figure 3E:
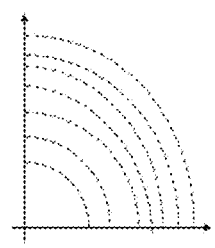
Figure 3G:
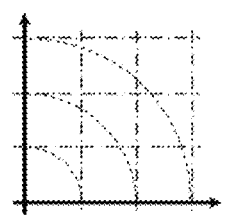
Figure 3B:
Figure 3D:
Figure 3F:
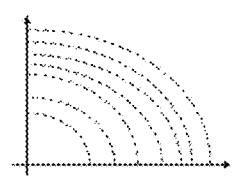

Because of these differences, the input data gathered by the first instance of the chemical sensing system (depicted in FIG. 3C) may differ from the input data gathered by the second instance of the chemical sensing system (depicted in FIG. 3D) when exposed to the same stimulus under the same conditions. Unsupervised learning, for example using the techniques described herein for identifying manifolds corresponding to varying concentrations of a single analyte, may be used to generate a representation Ω from the output signals obtained in each instance. Supervised learning techniques for domain adaptation may then be applied to map the representation Ω for each instance (e.g., as depicted in FIG. 3E and FIG. 3F) to a common output representation V (e.g., as depicted in FIG. 3G), instead of attempting to apply such techniques at the feature extraction step.

In some embodiments, the approach disclosed with regards to FIGS. 3A to 3G may enable a model trained using data acquired using a first chemical sensing system to be applied to data acquired using another chemical sensing system on which the model has not been trained. As described above, these two chemical sensing systems may differ due to normal manufacturing variations, or may include differing types of chemical sensor or differing models or versions of the same type of chemical sensor. In some embodiments, the encoded information from the two chemical sensing systems can be processed through separate instances of the same learning process, determining the representation Ω for each chemical sensing system via unsupervised or semi-supervised learning techniques before mapping these non-linearized output representations to the common output representation V.

Figure 4:
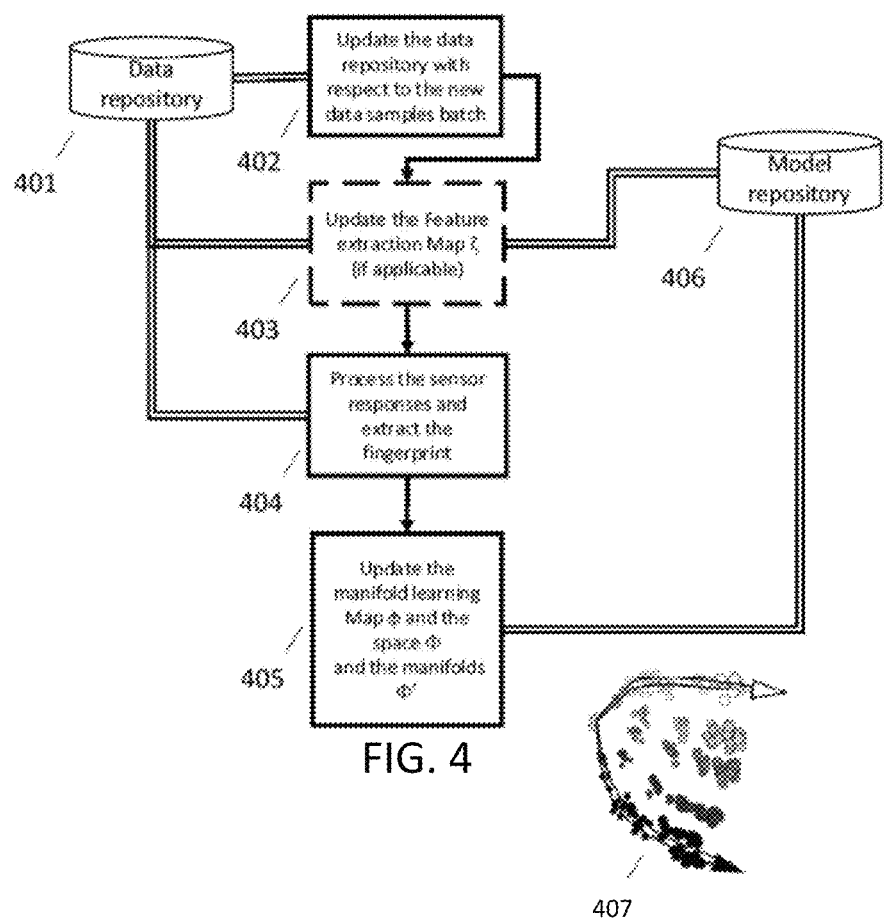
FIG. 4 depicts an exemplary process for learning mappings from signals output by sensors to a latent representation of these output signals.

FIG. 4 depicts an exemplary process 400 for learning mappings from signals output by sensors to a latent representation of these output signals. Process 400 can be performed on a chemical sensing system including a data repository 401, which may be a database hosted on a first computing device or any other suitable data structure stored on a storage device. The database may be configured to store output signals received from sensors. The database can also be configured to store intermediate values generated by the application of one of more mappings to the output signals. The chemical sensing system can include a model repository 406, which may be a database hosted on the first computing device or another computing device. The models stored can include at least some of the models described above, with regard to FIGS. 2A and 2B. For example, model repository 406 can be configured to store a model implementing mapping ζ from output signals to feature vectors and a model implementing mapping φ from feature vectors to latent vectors.

The chemical sensing system can be configured to acquire data (e.g., output signals) using a chemical sensing system, such as chemical sensing system 100, described above with regard to FIG. 1. In some embodiments, the chemical sensing system is configured to acquire the data in batches in act 402. Upon acquiring a batch of data, the chemical sensing system may be configured to determine whether an update criterion is satisfied. Satisfaction of this update criterion may indicate that the data in the new batch introduces new information. The chemical sensing system may therefore be configured to update one or more of mapping ζ and φ to reflect this new information. In some embodiments, satisfaction of the update criterion depends on a value of the mutual information between the new batch of data and the previously-received batch of data. In some embodiments, when the update criterion is satisfied, the chemical sensing system is configured to update the feature extraction map in act 403. As described above, the mapping ζ may be parameterized. The chemical sensing system may be configured to update mapping ζ by updating the parameters of mapping ζ using a machine learning technique in act 403. The updated parameters may then be stored in the model repository 406.

The chemical sensing system may be configured to process the received output signals using the updating mapping ζ to update representation Z with updated feature vectors in act 404. In some embodiments, the chemical sensing system can update the mapping φ using feature vectors in updated representation Z. As described above, mapping φ may be parameterized. The chemical sensing system may be configured to update mapping φ by updating the parameters of mapping φ using a machine learning technique in act 405. The updated parameters may then be stored in the model repository 406. The updated map φ may introduce a new subspace, manifold Φ' (updated latent representation 407), that is a representation of the information content of the dataset for the application of the learned maps.

Figure 5:
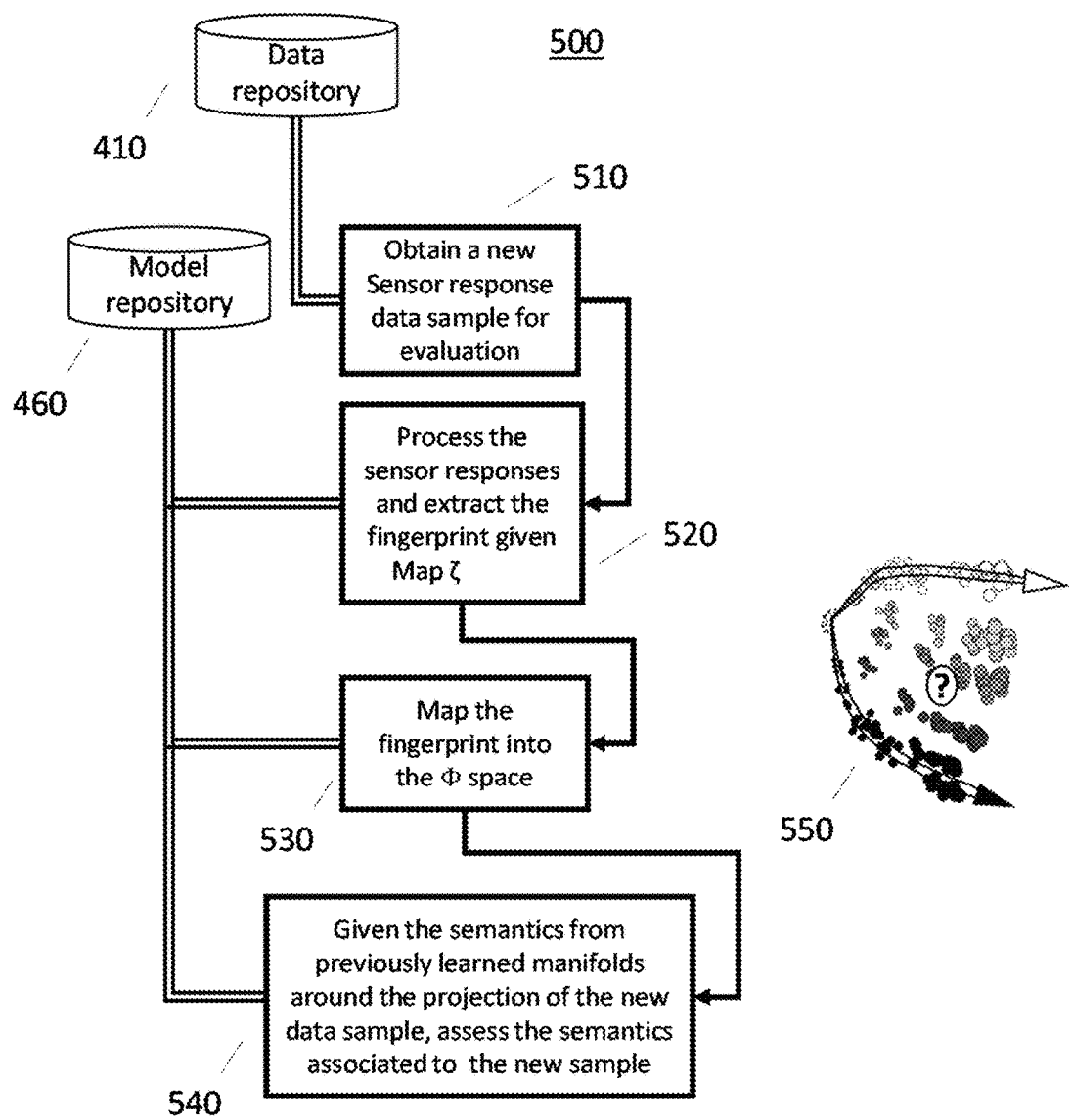
FIG. 5 depicts an exemplary process for using learned mappings to identify and quantify the chemicals within the sensor environment.

FIG. 5 depicts an exemplary process 500 for using learned mappings to identify and quantify the chemicals within the sensor environment. In act 510, a chemical sensing system may acquire output signals. The chemical sensing system may determine whether the acquired signals satisfy a storage criterion. Satisfaction of this storage criterion can indicate that the output signal introduces new information. The chemical sensing system may be configured to store the output signal, together with any contextual information, in data repository 410. In some embodiments, satisfaction of the storage criterion depends on a value of the mutual information between the acquired output signals and output signals already stored in data repository 410. The output signals stored in data repository 410 may be used for updating mappings, as described above with regard to FIG. 4. The chemical sensing system may then calculate a point in the Z representation, $\vec{z}$, from the output signals using a model stored in model repository 406 that implements the map ζ in act 520. The chemical sensing system may then calculate a point in the Φ space, $\vec{p}$, from the point $\vec{z}$ using a model stored in model repository 406 that implements the map φ in act 530.

The chemical sensing system may be configured to infer a composition of the environment corresponding to the value $\vec{p}$ in the Φ space in act 540. This inference can depend on semantics associated with points of manifold Φ (depicted as manifold 550 in FIG. 5) in a neighborhood of $\vec{p}$. For example, the chemical sensing system may be configured to identify labeled points within a predetermined distance of $\vec{p}$. Such labeled points may be associated with known concentrations of analytes. While the overall relationship between analyte concentrations and locations in the $\Phi$ space may be complex and non-linear, for a sufficiently small region around $\vec{p}$, the relationship may be approximately linear. Accordingly, the chemical sensing system may be configured to estimate analyte concentrations corresponding to $\vec{p}$ based on analyte concentrations associated with the labeled points within the predetermined distance of $\vec{p}$. In some embodiments, the chemical sensing system may be configured to interpolate concentrations for $\vec{p}$ based on these known concentrations.

Figure 6:
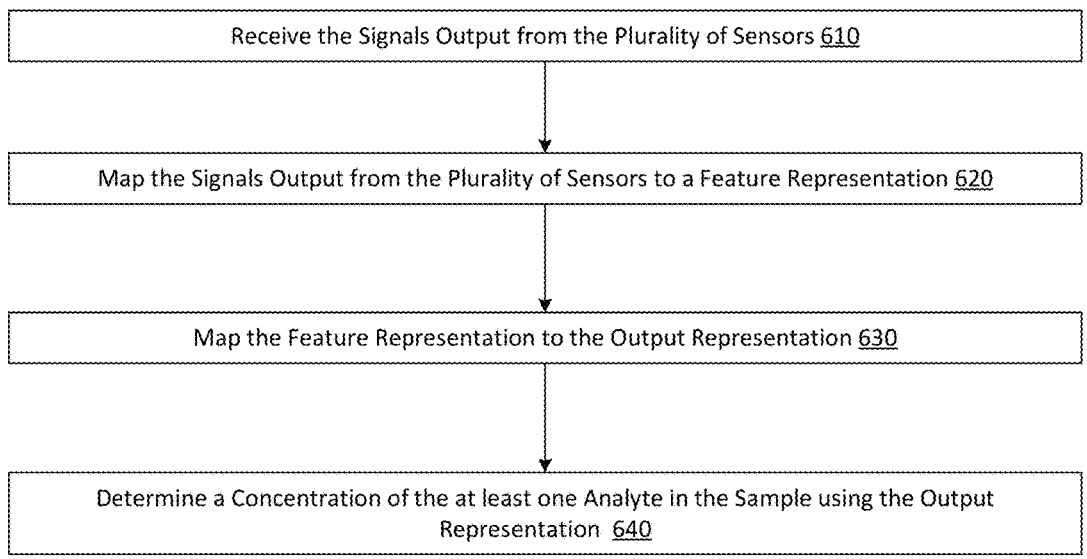
FIG. 6 depicts an exemplary process for determining a concentration of at least one analyte in a sample.

FIG. 6 depicts an exemplary process 600 for determining a concentration of at least one analyte in a sample. The process 600 may be implemented using at least some of the mappings described above with regard to FIGS. 2A and 2B. Process 600 may be implemented using a chemical sensing system. The chemical sensing system can include a sensor array (e.g., sensor array 120). The sensor array can include a plurality of sensors arranged on a substrate. A first sensor and a second sensor of the plurality of sensors can have different sensitivities to sense different analytes in a sample. In some instances, each of the plurality of sensors can be configured to output a signal in response to sensing an analyte. In some embodiments, the chemical sensing system can include a computing device. The computing device can include a processor and a memory configured to store data and instructions for performing one or more of the processes described herein. In some instances, the chemical sensing system is configured to determine a concentration of analytes in the sample based, at least in part, on the output signals generated by the sensors and a model relating the output signals or information derived from the output signals to the output representation V. The output representation V may have bases corresponding to the different analytes in the sample.

In act 610, the chemical sensing system receives signals output from the plurality of sensors. Each signal may include a time series of measurements, as described above with regard to FIGS. 2A and 2B. In some embodiments, the signals are received as they are generated (e.g., as a stream of data). In some embodiments, the signal is stored and subsequently provided to the chemical sensing system. In some embodiments, the signals are received from the sensors over a network. For example, the chemical sensing system containing the sensors may be located remote from the computing device processing the signal. In some embodiments, the chemical sensing system containing the sensors may be integrated with the computing device.

In act 620, a first model is used to map the signals output from the plurality of sensors to a feature representation Z. In some embodiments this mapping is non-linear. For example, a change in an analyte concentration in the sample results in a non-linear change in a location of a point in the feature representation. The chemical sensing system can be configured to perform this mapping using a first model relating the signals output from the plurality of sensors to a feature representation. The mapping may include an act of mapping from the output signals to response values. In some embodiments, an amplitude characteristic and/or a temporal characteristic of an output signal is mapped to each corresponding response value (e.g., a response value may be vector-valued, with one or more components corresponding to amplitude characteristics and one or more components corresponding to temporal characteristics). The amplitude characteristic may be, for example, a normalized change in an amplitude of the corresponding signal. The temporal characteristic may be, for example, a rise time or a fall time of an amplitude of the corresponding signal. These response values may then be weighted and combined to form feature vectors in the feature representation. In some embodiments, the weights may be the weights of a neural network that relate the response values to the feature representation. The neural network can be a recurrent neural network (or include recurrent neural network layers) a convolutional neural network (or include convolutional neural network layers) or another type of neural network. In this manner, a weighting can relate the response values to the feature representation.

In act 630, a second model is used to map the feature vectors corresponding to the output signals from the feature representation Z to an output representation V. The second model may include multiple sub-models that implement sub-mappings, as described above. In some embodiments, a first sub-model relates a feature representation Z to a latent representation $\Phi$. In some embodiments, latent representation $\Phi$ has a lower dimensionality than the feature representation. For example, as described above, the number of dimensions in feature representation Z can depend on the number of sensors in the sensor array and the number of features extracted from each sensor. The number of dimensions in latent representation $\Phi$ can depend on the number of relevant base analytes. For example, when the sensor array includes 32 sensors and a single feature is extracted from each output signal, feature representation Z can be a 32-dimensional space. When the chemical sensing system is configured to detect four relevant base analytes, the latent representation $\Phi$ can be a four-dimensional space.

A second sub-model can relate the latent representation $\Phi$ to a straightened orthogonal representation $\Omega$. In the straightened orthogonal representation $\Omega$, one-dimensional manifolds corresponding to varying concentrations of the same analyte are defined to have zero angle between them and one-dimensional manifolds corresponding to different analytes are orthogonal.

A third sub-model can relate the straightened orthogonal representation $\Omega$ to the output representation V. The location of points in the output representation V can be a linear function of the concentration of analytes in corresponding samples. The third sub-model can relate the straightened orthogonal representation to a non-linearized output representation U having standard bases associated with the base analytes. The third sub-model can implement this relationship according to a mapping $\tau$, as described herein. The third sub-model can also relate the non-linearized output representation U to the output representation V. The third sub-model can implement this relationship according to a mapping $\eta$, as described herein.

In act 640, a concentration of at least one analyte in the sample is determined using the output representation. In some embodiments, the chemical sensing system can determine the concentration of each relevant analyte based on the location of the point corresponding to the sample in the output representation. For example, when the output representation includes axes corresponding to four relevant base analytes, the location of a point in the output representation may be $[c_1\ c_2\ c_3\ c_4]$. In this example, $c_1$ is the concentration of the first base analyte, $c_2$ is the concentration of the second base analyte, $c_3$ is the concentration of the third base analyte, and $c_4$ is the concentration of the fourth base analyte. In some embodiments, the chemical sensing system can be configured to store, display, or provide the position in the output representation corresponding to the sample.

Figure 7:
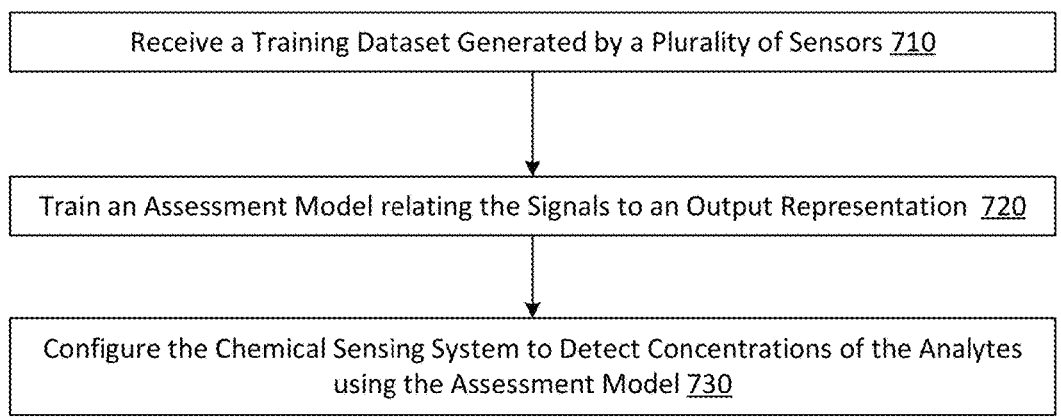
FIG. 7 depicts an exemplary process for configuring a chemical sensing system to detect concentrations of at least one analyte.

FIG. 7 depicts an exemplary process for configuring a chemical sensing system to detect concentrations of at least one analyte. In some embodiments, a training device includes a processor and a memory configured to store data and instructions for performing the disclosed embodiments. In some instances, the training device is configured to train an assessment model relating output signals generated by sensors in a sensor array (or information derived from such signals) to an output representation V having bases corresponding to base analytes. The chemical sensing system can then be configured to detect concentrations of the analytes using the trained assessment model. For example, the chemical sensing system can be configured to use the trained assessment model to relate output signals (or information derived from the output signals) to the output representation, as described above with regard to FIG. 6.

In some embodiments, the assessment model can include a set of models. In such embodiments, training using the training dataset may be performed over all models simultaneously. For example, the set of models may use the training data to generate estimated concentrations, which may be compared to known concentrations using labels in the training data to generate an error signal, which may be used to update all of the models. In various embodiments, a subset of the set of models may be trained simultaneously. For example, each model in the set of models can be trained individually using the training dataset. For example, the first two models in the set of models may be at least partially trained. These models can then generate output using the signals in the training dataset. This output can be used to train the next model in the set of models. In some embodiments, the set of models may undergo iterative training. In each iteration, each of the models may be trained using at least a portion of training dataset. Training of individuals models, subsets of the set of models, or the overall assessment model may continue until training time criteria and/or accuracy criteria are satisfied.

In act 710, a training dataset generated by a plurality of sensors is received by the training device. The sensors may have different sensitivities to sense different analytes in an environment. The sensors may be configured to output a signal in response to sensing the different analytes. In some embodiments, the training dataset may include $\vec{x}(t)$ as described above with regard to FIGS. 2A and 2B. For example, the training dataset may include one or more components of the tuple $\{D(t_i)=(t_i, C(t_i), \vec{x}(t_i), \vec{a}(t_i))\}$ in addition to the output signals $\vec{x}(t)$. In some embodiments, the training device is configured to receive the training dataset as it is being generated by the sensors (e.g., as a data stream). In some embodiments, the training device is configured to receive the training dataset after it is generated by the sensors (e.g., the training dataset is stored and is later provided to the training device). The training dataset may be received directly from one or more instances of the chemical sensing system, or indirectly from a database configured to store the training dataset. The training dataset may be received over a network, or from an instance of the chemical sensing system connected to the training device. In some embodiments, an instance of the chemical sensing system can include the training device, and the training may be performed by the chemical sensing system.

In act 720, an assignment model relating signals output by sensors (or information derived from the output signals) to the output representation V is trained by the training device. In some embodiments, training the assessment model includes generating a first model relating the signals output from the plurality of sensors to the feature representation Z. In some embodiments, the first model is implemented, at least in part, by one or more neural networks (e.g., a recurrent neural network, a convolutional neural network, or a neural network including recurrent and/or convolutional layers). Training the first model can include training weights of the neural network using the training dataset. In some embodiments, the first model is trained using an unsupervised learning technique (e.g., without relying on labeled training data).

In some embodiments, training the assessment model includes generating a second model relating feature representation Z to the output representation V. The second model can include multiple sub-models, which may be trained separately. In some embodiments, the mapping of feature representation Z to the output representation V includes associating bases in the straightened orthogonal representation with the analytes.

A first sub-model may relate the feature representation Z to a latent representation Φ. In some embodiments, a continuous manifold embedded in the feature representation Z contains the signals output from the plurality of sensors. The continuous manifold may have a dimensionality equal to the dimensionality of the latent representation Φ. Accordingly, the latent representation Φ may have a dimensionality less than the dimensionality of the feature representation Z. In some embodiments, the first sub-model includes a machine-learning model suitable for dimensionality reduction, such as the encoder of an autoencoder, the generator of a generative adversarial network, or a like model. The training device can be configured to train the first sub-model using the training dataset. In some embodiments, the training is performed using an unsupervised learning technique (e.g., without relying on labeled training data). In some embodiments, the first sub-model implements a non-parametric technique of dimensionality reduction (e.g., t-distributed stochastic neighbor embedding (t-SNE)).

In some embodiments, as described above with regard to FIGS. 2A and 2B, training the assessment model includes identifying manifolds corresponding to samples of varying concentrations of a same analyte. This training can proceed iteratively to identify one-dimensional manifolds associated with base analytes of varying concentrations in the feature representation Z using local gradient changes. The identification of these manifolds as associated with base analytes can be subsequently relied upon to generate models for straightening and orthogonalizing the latent representation Φ.

A second sub-model may relate the latent representation Φ to a straightened, orthogonal representation Ω. The second sub-model may include a straightening neural network. In some embodiments, the straightening neural network is implemented as a feedforward neural network that relates the latent representation to a straightened representation. The training device can be configured to train the straightening neural network using the training dataset and a loss function configured to penalize generation of non-zero angles between vectors output by the at least one neural network that correspond to samples of varying concentrations of a same analyte. The second sub-model may also include an orthogonalization neural network. In some embodiments, the orthogonalization neural network is implemented as a feedforward neural network that relates the straightened representation to a straightened, orthogonal representation. The training device can be configured to train the orthogonalization neural network using the training dataset and a loss function configured to penalize generation of non-orthogonal vectors output by the orthogonalization neural network that correspond to samples of different analytes. Training the second sub-model can include training at least one of the straightening neural network or the orthogonalization neural network using an unsupervised learning technique (e.g., without relying on labels associated with the training data). In some embodiments, this training relies on associations determined using local gradient changes.

A third sub-model may relate the straightened orthogonal representation Ω to the output representation V. In some embodiments, the training device is configured to use labels in the training data to associate bases in the straightened orthogonal representation with the base analytes. For example, the training device may identify an analyte associated with a basis using labels associated with one or more points lying on or near the basis. The training device can then generate an introduction model that introduces the associated bases onto the standard bases of a non-linearized output representation U. In some embodiments, the training device generates a linearizing model that linearizes the non-linearized output representation U using concentrations indicated in labels associated with the training data. In some embodiments, the linearizing model that linearizes the non-linearized output representation U includes a neural network. In some embodiments, this neural network is implemented as a feedforward neural network. The training device can be configured to train the neural network to linearize the non-linearized output representation U using the training data and concentration values corresponding to the training data.

In some embodiments, one or more of the models described above may be trained by a device other than the training device. For example, the training device may be configured to generate the first model and the first and second sub-models. These models may collectively relate the output signals to a straightened orthogonal representation Ω. The training device may then receive the third sub-model relating the straightened orthogonal representation Ω to the output representation V. In this manner, models may be reused, or only generated as necessary. As an additional example, as indicated above with regard to FIGS. 3A to 3G, one or more training devices may be configured to generate models relating output signals generated by different instances of a chemical sensing system to a common representation (e.g., non-linearized output representation U). Another model usable with each of the different instances of the chemical sensing system can then relate the non-linearized output representation U to output representation V.

In act 730, the chemical sensing system can be configured to detect concentrations of the analytes using the assessment model. For example, the training device, or another device, can cause the assessment model to be stored in a memory of the chemical sensing system. The chemical sensing system can then be configured to use the assessment model to map output signals received from sensors to the output representation V.

FIGS. 8A to 8E depict empirical test data for three analytes (acetone, ethanol and toluene) mapped to various representations using models trained according to the disclosed embodiments.

The dataset includes the output signal received from the sensing elements in the chemical sensing system to 1200 chemical samples. The chemical samples including samples of pure acetone, ethanol or toluene at various concentrations as the base analytes. The chemical samples also included mixtures of acetone, ethanol and/or toluene at various proportions and various total concentrations. Each output signal included 32 sequences of time-series data, each sequence corresponding to one of the 32 sensing elements.

The samples were introduced into a 1.5 L chamber in which the chemical sensing system was mounted. 10 samples of acetone, ethanol and toluene each were collected at concentrations varying from 2.5 uL to 25 uL. Mixtures of (Acetone, Ethanol), (Acetone, Toluene), (Toluene, Ethanol) and (Acetone, Toluene, Ethanol) in which the proportion of each chemical varied from 0% to 100% (0%, 17%, 25%, 33%, 50%, 66%, 75%, and 100%) were introduced to the chamber with total concentration varying from 2.5 uL to 25 uL. Per each mixture and at various concentrations, 10 samples were collected in the dataset to represent the semantic with the local distribution for each chemical composition.

Figure 8A:
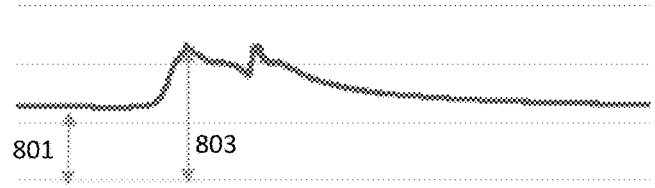
FIGS. 8A to 8F depict empirical test results for three analytes mapped to various representations using models trained according to some embodiments.

FIG. 8A depicts an exemplary transient response of a sensing element to one of the chemical compositions tested. The extremum value of the transient response is indicated as 803 and the baseline value of the transient response is indicated as 801. In this example, the mapping ζ includes only a descriptor f being the value "1" subtracted from the extremum value on the transient response, α, divided by the baseline vector, β, which is calculated for each cycle.

$$f = \begin{bmatrix} f_1 \\ f_2 \\ \vdots \\ f_{32} \end{bmatrix}, \alpha = \begin{bmatrix} \alpha_1 \\ \alpha_2 \\ \vdots \\ \alpha_{32} \end{bmatrix}, \beta = \begin{bmatrix} \beta_1 \\ \beta_2 \\ \vdots \\ \beta_{32} \end{bmatrix} \text{ where } f_i = \frac{\alpha_i}{\beta_i} - 1$$

As the chemical sensing system included 32 sensing elements, the feature vector corresponding to each environment include 32 values. The feature representation Z was a 32-dimensional space. Disposed in this 32-dimensional space were 1200 values corresponding to the 1200 samples.

Figure 8B:
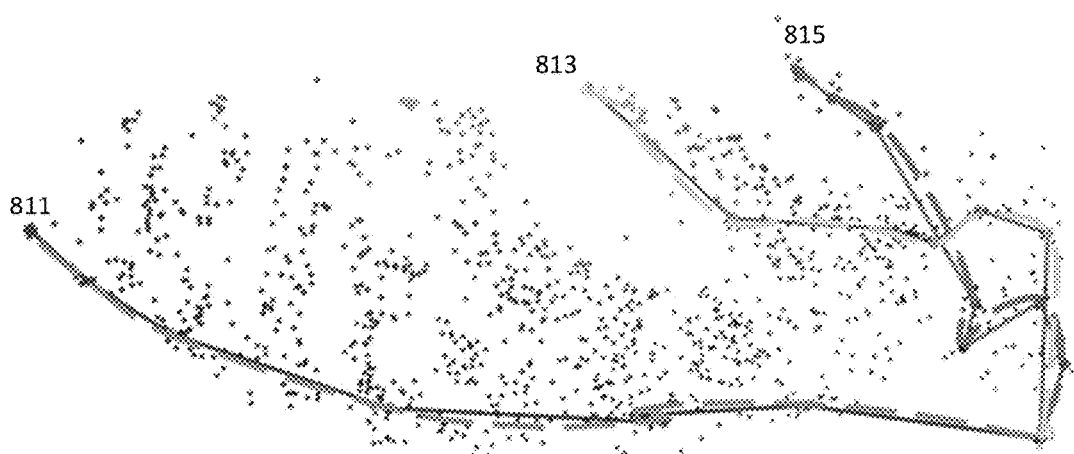

In FIGS. 8B to 8F, the values of the points in each representation are presented by small circles. Each of the three lines indicate points corresponding to varying concentrations of one of three base analytes (acetone, ethanol, toluene). FIG. 8B depicts an exemplary latent representation Φ generated from the feature representation Z according to a mapping φ. The mapping φ was generated using t-distributed stochastic neighbor embedding (t-SNE) to learn a reduced three-dimension space 1. As t-SNE preserves the locality of close concepts in the original space after reducing the dimension, when two points are close to (or far from) each other in the original thirty-two-dimensional feature representation Z, the corresponding two points will remain close to (or far from) each other in the three-dimension latent representation Φ. In the dataset, for each unique proportion and concentration of analytes there are multiple output signals. These output signals map to correlated points (close but not in the exact same location) in the thirty-two-dimensional space, Z, and the equivalent three-dimensional space, Φ. In FIG. 8B, the manifold 815 connects the median values of samples of pure acetone of varying concentrations, the manifold 813 connects the median values of samples of pure ethanol of varying concentrations, and the manifold 811 connects the median values of samples of pure toluene of varying concentrations. The broken lines are curves fitted on the points related to each of the base analytes.

Figure 8C:
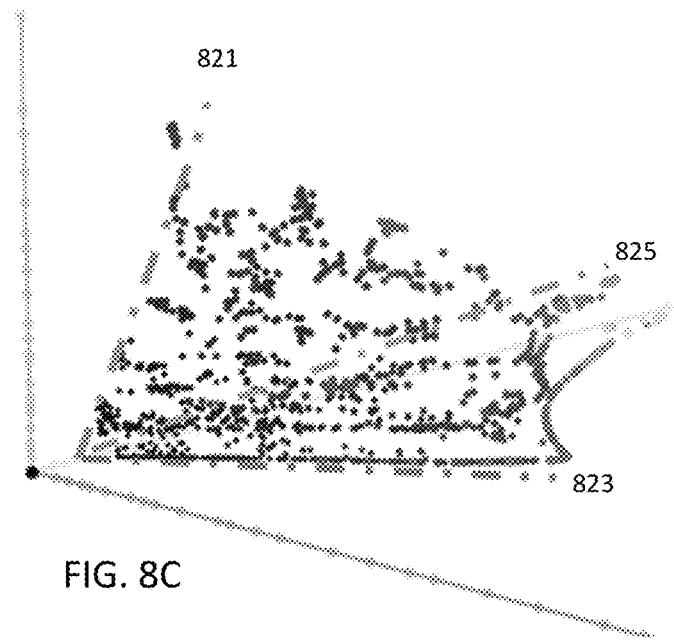

FIG. 8C depicts an exemplary straightened representation $\Psi$ generated from the latent representation $\Phi$ according to a mapping $\psi$. In this example, the axes were identified for each base analyte (e.g., axis 821 for toluene, axis 825 for ethanol, and axis 823 for acetone). This identification can be performed using the iterative process of identifying exterior points in the manifold described herein. As there are three base analytes in the dataset, three axes can be identified. To straighten the axes, a line equation is calculated for each axis. These line equations can be constrained such that they do not all lie within a plane and an origin of all the line equations lie on or near a point corresponding to the absence of analytes in the sample. Each point associated with a base analyte is then mapped to a point on the corresponding line for that analyte. This mapping $\psi$ can be generated using a neural network trained to straighten the axes and unfold the manifold. After the training is done, the mapping $\psi$ is applied to the points in the latent representation $\Phi$ to generate corresponding points in the transformed space $\Psi$.

Figure 8D:
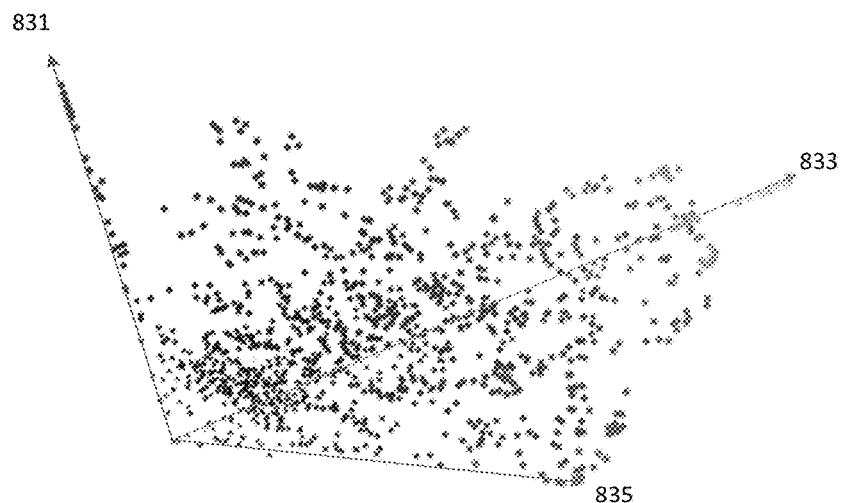

FIG. 8D depicts an exemplary straightened, orthogonal representation $\Omega$ generated from the straightened representation $\Psi$ according to a mapping $\omega$. In this example, the axes of $\Psi$ have been straightened, but are not (at least in this example) orthogonal. The chemical sensing system can be configured to generate orthogonal axes according to the following process. In a first act of the process, a first axis $y_1$ (depicted as axis 831) is selected. In this non-limiting example, the selected axis 831 is not modified. A second axis $y_2$ is then selected and a mapping from the second axis $y_2$ to a target axis $y'_2$ (axis 833), orthogonal to the first axis 831, is then determined. The mapping of $y_2$ to axis 833 may also have the effect of mapping the third axis $y_3$ to $y'_3$. The remaining axis $y_3$ is then selected and a mapping from $y'_3$ to a target axis 835 is determined. Throughout this process, target locations are generated for the points lying on axes $y_2$ and $y_3$. A neural network may then be trained to implement the mapping $\omega$, which may map the points lying on axes $y_2$ and $y_3$ to the target locations. This neural network can then be used to calculate locations in straightened, orthogonal representation $\Omega$ correspond to the points in straightened representation $\Psi$.

Figure 8E:
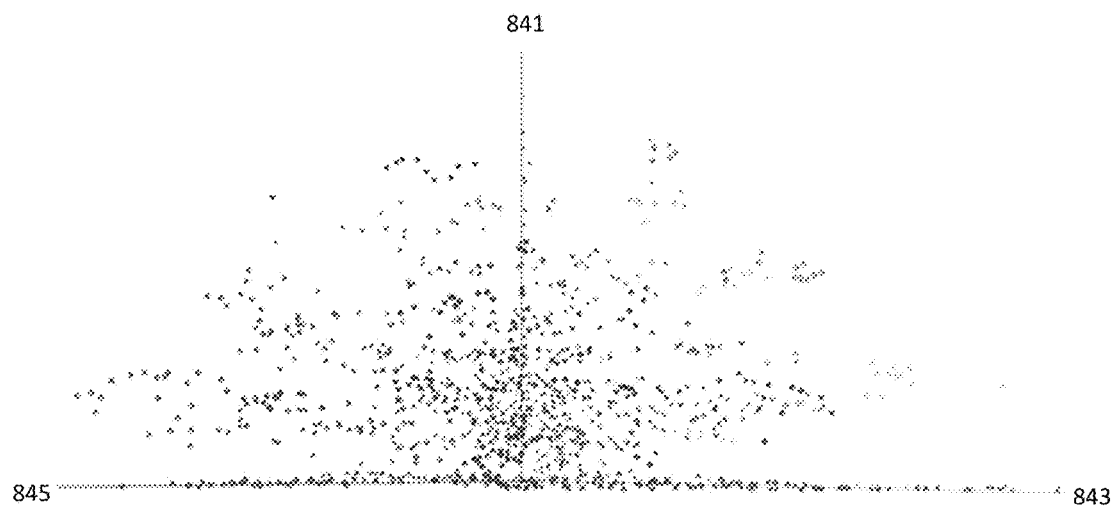

FIG. 8E depicts an exemplary standard basis representation U generated from a straightened, orthogonal representation $\Omega$ according to a mapping $\tau$. In this example, the axes of $\Omega$ are orthogonal but are not (at least in this example) aligned with the standard bases of $\mathbb{R}^M$ (e.g., axis 841, axis 843, and axis 845). Using the labels associated with the data, the system can determine a projection from $\Omega$ to U that aligns each axis of $\Omega$ with a corresponding standard basis in U. For example, if the x-axis in U corresponds to ethanol, the mapping $\tau$ may project the axis in $\Omega$ corresponding to ethanol to the x-axis in U (e.g., axis 843).

Figure 8F:
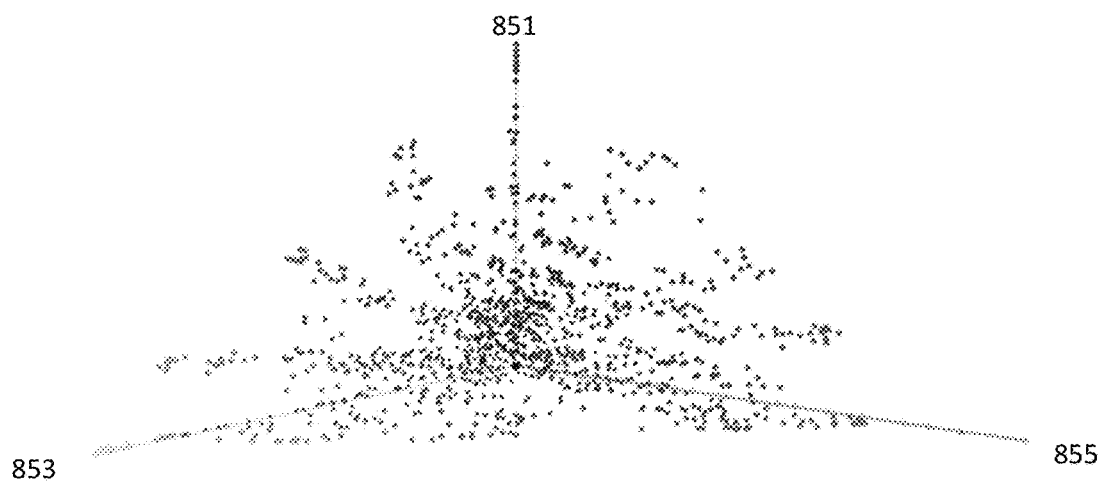

FIG. 8F depicts an exemplary output representation V generated from standard basis representation U according to a mapping $\eta$. Using the concentrations and proportions included in the labels associated with the data, target points in output representation V are determined for each point in standard basis representation U. A neural network can be trained to implement the mapping $\eta$ that transforms the points in standard basis representation U to the target points in output representation V.

Once the mappings $\tau$, $\eta$, $\omega$, $\psi$, $\varphi$, and $\zeta$, have been determined, the chemical sensing system can be configured with these mappings. For example, models and parameters implementing these mappings can be saved to a memory of the chemical sensing system. The chemical sensing system can be configured to apply the stored models according to the stored parameters to implement these mappings, mapping the output sample received from the sensor array to a point in the output representation with clearly defined semantics.

The foregoing description of implementations provides illustration and description, but is not intended to be exhaustive or to limit the implementations to the precise form disclosed. Modifications and variations are possible in light of the above teachings or may be acquired from practice of the implementations. In other implementations the methods depicted in these figures may include fewer operations, different operations, differently ordered operations, and/or additional operations. Further, non-dependent blocks may be performed in parallel. The chemical sensing system depicted in FIG. 1 is similarly intended to be exemplary.

It will be apparent that example aspects, as described above, may be implemented in many different forms of software, firmware, and hardware in the implementations illustrated in the figures. Further, certain portions of the implementations may be implemented as a "module" that performs one or more functions. This module may include hardware, such as a processor, an application-specific integrated circuit (ASIC), or a field-programmable gate array (FPGA), or a combination of hardware and software.

Even though particular combinations of features are recited in the claims and/or disclosed in the specification, these combinations are not intended to limit the disclosure of the specification. In fact, many of these features may be combined in ways not specifically recited in the claims and/or disclosed in the specification. Although each dependent claim listed below may directly depend on only one other claim, the disclosure of the specification includes each dependent claim in combination with every other claim in the claim set.

No element, act, or instruction used in the present application should be construed as critical or essential unless explicitly described as such. Also, as used herein, the article "a" is intended to include one or more items. Where only one item is intended, the term "one" or similar language is used. Further, the phrase "based on" is intended to mean "based, at least in part, on" unless explicitly stated otherwise. Approximately, as used herein, is intended to mean within 10% of a nominal value, consistent with the understanding of one of skill in the art and unless otherwise specified.

What is claimed is:

1. A chemical sensing system, comprising:
   a plurality of sensors arranged on at least one substrate, wherein a first sensor and a second sensor of the plurality of sensors have different sensitivities to sense at least one analyte in a sample, each of the plurality of sensors being configured to output a signal in response to sensing the at least one analyte; and
   a computer processor programmed to:
      receive the signals output from the plurality of sensors;
      determine a concentration of the at least one analyte in the sample by:
         providing the received signals as input to a first model trained to relate the signals output from the plurality of sensors to a feature representation to generate feature representation values;
         providing the feature representation values as input to a second model trained to relate the feature representation to a latent representation to generate latent representation values, the latent representation having a lower dimensionality than the feature representation;
providing the latent representation values as input to a third model trained to relate the latent representation to a straightened orthogonal representation to generate straightened orthogonal representation values, wherein:
one-dimensional manifolds in the straightened orthogonal representation corresponding to varying concentrations of a same analyte have zero angle between them; and
one-dimensional manifolds in the straightened orthogonal representation corresponding to different analytes are orthogonal;
providing the straightened orthogonal representation values as input to a fourth model trained to relate the straightened orthogonal representation to an output representation having bases corresponding to analytes, the analytes including the at least one analyte; and
determining the concentration of the at least one analyte in the sample based on an output of the fourth model; and
provide an indication of the determined concentration of the at least one analyte in the sample to a user.

2. The chemical sensing system of claim 1, wherein the first model comprises:
a mapping from the signals to response values; and
a weighting relating the response values to the feature representation.

3. The chemical sensing system of claim 2, wherein the weighting comprises weights of a recurrent neural network or convolutional neural network that relate the response values to the feature representation.

4. The chemical sensing system of claim 2, wherein the mapping assigns to each response value an amplitude characteristic and/or a temporal characteristic of a corresponding signal.

5. The chemical sensing system of claim 4, wherein the amplitude characteristic comprises a normalized change in an amplitude of the corresponding signal.

6. The chemical sensing system of claim 4, wherein the temporal characteristic comprises a rise time or a fall time of an amplitude of the corresponding signal.

7. The chemical sensing system of claim 1, wherein a change in a location of a point in the feature representation corresponding to an analyte concentration in the sample is a non-linear function of a change in the analyte concentration in the sample.

8. The chemical sensing system of claim 1, wherein each signal comprises a time series of measurements.

9. The chemical sensing system of claim 1, wherein
the first model and the second model are device-specific models; and
the third model and the second model are device-independent models.

10. A chemical sensing system, comprising:
at least one computer processor; and
at least one computer readable medium including instructions that, when executed by the at least one computer processor, cause the chemical sensing system to perform a training process, the training process comprising:
receiving a training dataset including values associated with signals output from a plurality of sensors having different sensitivities to sense at least one analyte in a sample, each of the plurality of sensors configured to output the signal in response to sensing the at least one analyte;
training a set of models using the training dataset by:
training a first model to relate the signals output from the plurality of sensors to a feature representation;
training a second model to relate the feature representation to a latent representation, the latent representation having a lower dimensionality than the feature representation;
training a third model to relate the latent representation to a straightened orthogonal representation, wherein:
one-dimensional manifolds in the straightened orthogonal representation corresponding to varying concentrations of a same analyte have zero angle between them; and
one-dimensional manifolds in the straightened orthogonal representation corresponding to different analytes are orthogonal; and
training a fourth model to relate the straightened orthogonal representation to the output representation having bases corresponding to analytes; and
configuring the chemical sensing system to detect a concentration of the least one analyte in the sample using the trained set of models.

11. The system of claim 10, wherein training the first model comprises updating weights in a recurrent neural network or a convolutional neural network.

12. The system of claim 10, wherein the training dataset does not include labels for at least some of the values in the training set and wherein training the first model comprises training the first model without using the labels.

13. The system of claim 10, wherein training the second model comprises training at least a portion of an autoencoder or generative adversarial network.

14. The system of claim 10, wherein:
a continuous manifold embedded in the feature representation contains the signals output from the plurality of sensors, the continuous manifold having a dimensionality equal to the dimensionality of the latent representation; and
the second model relates the continuous manifold to the latent representation.

15. The system of claim 10, wherein training the set of models using the training dataset further comprises automatically identifying manifolds corresponding to samples of varying concentrations of a same analyte using local gradient changes in the feature representation.

16. The system of claim 10, wherein training the fourth model comprises associating bases in the straightened orthogonal representation with the analytes.

17. The system of claim 10, wherein training the fourth model comprises:
associating bases in the straightened orthogonal representation with the analytes using labels in the training data;
generating an introduction model that introduces the associated bases onto standard bases of a non-linearized output representation; and
generating a linearizing model that linearizes the non-linearized output representation using concentrations in the training dataset corresponding to the signals output from the plurality of sensors.

18. The system of claim 17, wherein the linearizing model comprises at least one feedforward neural network trained to linearize the non-linearized output representation using the signals output from the plurality of sensors and corresponding concentration values in the training dataset.

19. The system of claim 10, wherein training the first model and/or the second model comprises:
receiving a device-specific model trained using information acquired by a device other than the chemical sensing device; and
retraining the device-specific model using at least a portion of the training dataset.

20. A chemical sensing method, comprising:
receiving, by a chemical sensing system, signals output from a plurality of sensors arranged on at least one substrate, wherein a first sensor and a second sensor of the plurality of sensors have different sensitivities to sense at least one analyte in a sample, each of the plurality of sensors being configured to output a signal in response to sensing the at least one analyte;
determining, by the chemical sensing system, a concentration of the at least one analyte in the sample by:
providing the received signals as input to a first model trained to relate the signals output from the plurality of sensors to a feature representation to generate feature representation values;
providing the feature representation values as input to a second model trained to relate the feature representation to a latent representation to generate latent representation values, the latent representation having a lower dimensionality than the feature representation;
providing the latent representation values as input to a third model trained to relate the latent representation to a straightened orthogonal representation to generate straightened orthogonal representation values, wherein:
one-dimensional manifolds in the straightened orthogonal representation corresponding to varying concentrations of a same analyte have zero angle between them; and
one-dimensional manifolds in the straightened orthogonal representation corresponding to different analytes are orthogonal;
providing the straightened orthogonal representation values as input to a fourth model trained to relate the straightened orthogonal representation to an output representation having bases corresponding to analytes, the analytes including the at least one analyte; and
determining the concentration of the at least one analyte in the sample based on an output of the fourth model; and
provide, by the chemical sensing system, an indication of the determined concentration of the at least one analyte in the sample to a user.

21. The method of claim 20, wherein the first model comprises:
a mapping from the signals to response values; and
a weighting that relates the response values to the feature representation.

22. The method of claim 21, wherein the mapping assigns, to each response value, a normalized change in an amplitude of a corresponding signal and/or a rise time or a fall time of an amplitude of the corresponding signal.

23. The method of claim 20, wherein a change in a location of a point in the feature representation corresponding to an analyte concentration in the sample is a non-linear function of a change in the analyte concentration in the sample.

24. The method of claim 20, wherein
the first model and the second model are device-specific models; and
the third model and the second model are device-independent models.

25. A computer-implemented training method, comprising:
receiving a training dataset including values associated with signals output from a plurality of sensors having different sensitivities to sense at least one analyte in a sample, each of the plurality of sensors configured to output the signal in response to sensing the at least one analyte;
training, using at least one computer processor, a set of models using the training dataset by:
training a first model to relate the signals output from the plurality of sensors to a feature representation;
training a second model to relate the feature representation to a latent representation, the latent representation having a lower dimensionality than the feature representation;
training a third model to relate the latent representation to a straightened orthogonal representation, wherein:
one-dimensional manifolds in the straightened orthogonal representation corresponding to varying concentrations of a same analyte have zero angle between them; and
one-dimensional manifolds in the straightened orthogonal representation corresponding to different analytes are orthogonal; and
training a fourth model to relate the straightened orthogonal representation to the output representation having bases corresponding to analytes; and
configuring a chemical sensing system to detect a concentration of the least one analyte in the sample using the trained set of models.

26. The method of claim 25, wherein:
training the first model comprises updating weights in a recurrent neural network or convolutional neural network;
training the second model comprises updating weights in at least a portion of an autoencoder or generative adversarial network; and
training the fourth model comprises updating weights in at least one feedforward neural network.

27. The method of claim 25, wherein:
a continuous manifold embedded in the feature representation contains the signals output from the plurality of sensors, the continuous manifold having a dimensionality equal to the dimensionality of the latent representation; and
the second model relates the continuous manifold to the latent representation.

28. The method of claim 25, wherein training the set of models using the training dataset further comprises automatically identifying manifolds corresponding to samples of varying concentrations of a same analyte using local gradient changes in the feature representation.

29. The method of claim 25, wherein training the fourth model comprises:
associating bases in the straightened orthogonal representation with the analytes using labels in the training data;
generating an introduction model that introduces the associated bases onto standard bases of a non-linearized output representation; and
generating a linearizing model that linearizes the non-linearized output representation using concentrations in the training dataset corresponding to the signals output from the plurality of sensors.

30. The method of claim 25, wherein training the first model and/or the second model comprises:
receiving a device-specific model trained using information acquired by a device other than the chemical sensing device; and
retraining the device-specific model using at least a portion of the training dataset.

* * * * *